United States Patent
Barnea

(10) Patent No.: US 9,097,725 B2
(45) Date of Patent: Aug. 4, 2015

(54) COMPOSITIONS AND METHODS FOR MODULATING THE IMMUNE SYSTEM

(71) Applicant: BioIncept, LLC, Cherry Hill, NJ (US)

(72) Inventor: Eytan R. Barnea, Cherry Hill, NJ (US)

(73) Assignee: BIOINCEPT, LLC, Cherry Hill, NJ (US)

( * ) Notice: Subject to any disclaimer, the term of this patent is extended or adjusted under 35 U.S.C. 154(b) by 0 days.

(21) Appl. No.: 13/909,047

(22) Filed: Jun. 3, 2013

(65) Prior Publication Data

US 2014/0004545 A1    Jan. 2, 2014
US 2015/0125886 A9    May 7, 2015

Related U.S. Application Data

(63) Continuation of application No. 12/786,290, filed on May 24, 2010, now Pat. No. 8,454,967, which is a continuation of application No. 11/381,818, filed on May 5, 2006, now Pat. No. 7,723,290, and a continuation-in-part of application No. 10/971,760, filed on Oct. 22, 2004, now Pat. No. 8,222,211, and a continuation-in-part of application No. 11/110,990, filed on Apr. 20, 2005, now Pat. No. 7,723,289.

(60) Provisional application No. 60/765,400, filed on Feb. 3, 2006, provisional application No. 60/765,393, filed on Feb. 3, 2006, provisional application No. 60/765,398, filed on Feb. 3, 2006, provisional application No. 60/746,511, filed on May 5, 2006, provisional application No. 60/513,370, filed on Oct. 22, 2003.

(51) Int. Cl.
*A61K 39/395* (2006.01)
*G01N 33/68* (2006.01)
*A61K 38/17* (2006.01)

(52) U.S. Cl.
CPC ........ *G01N 33/6854* (2013.01); *A61K 38/1709* (2013.01)

(58) Field of Classification Search
None
See application file for complete search history.

(56) References Cited

U.S. PATENT DOCUMENTS 5,646,003 A  *  7/1997  Barnea et al. ................ 435/7.24
5,981,198 A  *  11/1999  Barnea et al. ................ 435/7.23

FOREIGN PATENT DOCUMENTS

WO    WO 03004601 A2  *  1/2003
WO    WO 2004053086 A2  *  6/2004

OTHER PUBLICATIONS

Rose et al., Manual of Clinical Laboratory Immunology, 5th edition, 1997, ASM Press, pp. 20-29.*
Campbell A.M., Monoclonal Antibody Technology, Elsevier Science Publishing Company Inc., 1984, pp. 1-32.*

* cited by examiner

*Primary Examiner* — Michael Szperka
(74) *Attorney, Agent, or Firm* — Pepper Hamilton LLP

(57) ABSTRACT

A novel class of embryo derived peptides are described (Pre-implantation factor) that were generated synthetically and were tested on peripheral blood immune cells and shown to block activated but not basal immunity, inhibiting cell proliferation and creating a $T_H2$ type cytokine bias, in addition PIF enhance endometrial receptivity by increasing adhesion molecules expression. PIF biological activity appears to be exerted by specific binding to inducible receptors present on the several white cell lineages. PIF peptides, which are immune modulators therefore may have diagnostic and non toxic therapeutic applications in improving fertility, reducing pregnancy loss as well may be useful when administered for the treatment of autoimmune diseases and for prevention xenotransplants rejection.

12 Claims, 10 Drawing Sheets

COMPOSITIONS AND METHODS FOR MODULATING THE IMMUNE SYSTEM

This application is a continuation of U.S. application Ser. No. 12/786,290, entitled "Compositions and Methods for Modulating the Immune System," filed May 24, 2010, which is a continuation of U.S. application Ser. No. 11/381,818, entitled "Compositions and Methods for Modulating the Immune System," filed May 5, 2006, now U.S. Pat. No. 7,723,290, issued May 25, 2010, which claims priority to U.S. Provisional Application Ser. No. 60/765,400, entitled "Characterization of Preimplantation Factor 1 (PIF-11): An Embryo-Derived Peptide with Immune Modulatory Properties", filed Feb. 3, 2006, U.S. Provisional Application Ser. No. 60/765,393, entitled "PIF-1: An Embryo-Derived Peptide Prevents Autoimmune Disease Development in Preclinical Trials," filed Feb. 3, 2006; U.S. Provisional Application Ser. No. 60/765,398, entitled "GVHD Therapy In Cancer Patients Using PIF (Preimplantation Factor), A Non Toxic Embryo-Derived Immunemodulatory Peptide," filed Feb. 3, 2006; and U.S. Provisional Application Ser. No. 60/746,511, entitled "PIF-1 Induced Effects on PBMC Genome Alone and Following Exposure to CD3MAB/CD28MAB," filed May 5, 2006. U.S. application Ser. No. 11/381,818 is also a continuation-in-part of U.S. application Ser. No. 10/971,760, entitled "Methods of Administering PIF Agonist Peptides and Uses Thereof," filed Oct. 22, 2004, now U.S. Pat. No. 8,222,211, issued Jul. 17, 2012, which claims priority to U.S. Provisional Application Ser. No. 60/513,370, entitled "PIF Peptides Biologic Activities, Site of Action, and the Antibody to Detect PIF," filed Oct. 22, 2003. U.S. application Ser. No. 11/381,818 is also a continuation-in-part of U.S. application Ser. No. 11/110,990, entitled "PIF Tetrapeptides," filed Apr. 20, 2005, now U.S. Pat. No. 7,723,289, issued May 25, 2010, which is a continuation-in-part of U.S. application Ser. No. 10/971,760. U.S. application Ser. No. 12/786,290 is also a continuation-in-part of U.S. application Ser. No. 11/110,990. All aforementioned applications are herein incorporated by reference in their entireties.

BACKGROUND

Mammalian pregnancy is a unique physiological event in which the maternal immune system interacts with the fetus in a very efficient manner, beneficial for both parties. Pregnancy is an immune paradox, displaying no graft vs. host or host vs. graft effect. The factors involved in this phenomenon are not yet fully elucidated although they have been extensively studied. The novel embryo-derived factor, preimplantation factor (PIF-1), may cause immune tolerance of pregnancy by creating maternal recognition of pregnancy shortly after fertilization. Synthetic PIF-1 replicated the native peptide's effect and exerted potent immune modulatory effects on activated PBMC proliferation and cytokine secretion, acting through novel sites on PBMC and having an effect which is distinct from known immune-suppressive drugs.

There is evidence that several autoimmune diseases, including multiple sclerosis and rheumatoid arthritis, undergo remission during pregnancy, supporting the view that there are unique protective mechanisms operative during that time period. This is particularly remarkable because the host/mother is simultaneously being exposed to a semi- or total allograft (donor embryo) without adverse immune effects.

Allogeneic bone marrow transplantation (BMT) is a well-established treatment for malignant and non-malignant hematological diseases, and is performed in tens of thousands of patients each year. Mature donor T cells within the stem cell graft are the main mediators of the beneficial immune effects, but they are also responsible for the induction of graft-versus-host disease (GVHD), the major cause of morbidity and mortality in BMT patients. GVHD occurs when transplanted donor-derived T cells recognize proteins expressed by recipient antigen-presenting cells. Consequently, this recognition induces donor T-cell activation, proliferation, and differentiation, leading to a cellular and inflammatory attack on recipient target tissues. Acute or chronic GVHD occurs within a 100-day period post-BMT that leads to dermatitis, enteritis, and hepatitis. The treatment of GVHD continues to be a challenge. To eliminate undesirable host-derived hematopoietic elements before BMT, patients have traditionally been treated with myeloablative conditioning regimens involving high-dose chemotherapy and total-body radiation. Up until now, standard GVHD prophylaxis and therapy uses immune suppressive drugs (steroids and Cyclosporin A), that place patients in danger of opportunistic infections and tumor relapse. Numerous agents have been evaluated for GVHD, unfortunately with poor outcome. Ideally, prophylaxis of BMT patients by immune modulation would allow transplant acceptance, while maintaining the ability to protect against pathogens or cancer.

Type 1 (insulin-dependent) diabetes (TIDM) is caused by autoimmune destruction of the insulin-producing pancreatic beta cells. TIDM etiology is multifactorial, complex, and involves a combination of genetic, environmental, and immunological influences. TIDM is a progressive, asymptomatic decline in beta cell function until hyperglycemia develops. Near total beta-cell destruction may not be universal, and therefore therapeutic measures that stop destruction and perhaps lead to organ recovery could bring to major advances in TIDM management. TIDM prevention is currently suboptimal, and most current therapies aim at controlling glucose levels using insulin, or (rarely) by islet transplants. There are also attempts to initiate immune therapies using (anti-CD3 antibodies, and anti-thymocyte globulin) which aim to block the autoimmune cascade when combined with repair/regeneration of beta cells (e.g., glulisine, glucagon-like-peptide-1 (GLP-1), extendin-4), and Dia-Pep277 with limited success.

Multiple sclerosis (MS) is a progressive debilitating autoimmune disease of the central nervous system that has a complex etiology where genetic predisposition may be coupled with early childhood viral exposure. Consequently, there is a gradual destruction of the myelin sheath that causes motor, autonomic, sensory dysfunction that may lead to paralysis. Current therapies are based on limiting the damage by using steroids and interferon, Copaxone and monoclonal antibodies, with limited success. An optimal therapy would reverse the neural damage by blocking the autoimmune cascade while allowing for myelin sheath repair. The experimental autoimmune encephalitis (EAE) model is widely used currently to examine experimental treatments for MS.

Ulcerative colitis (UC) and Crohn's disease (CD), the primary constituents of inflammatory bowel disease (IBD), are precipitated by a complex interaction of environmental, genetic, and immunoregulatory factors. Higher rates of IBD are seen in northern, industrialized countries. IBD's are chronic inflammatory disorders of the gastrointestinal tract. Although the etiology is incompletely understood, initiation and aggravation of the inflammatory process seem to be due to a massive local mucosal immune response. Cytokine-mediated impairment of viability and metabolic function of epithelial cells has been suggested as a possible early pathogenic event in the development of inflammatory bowel disease (IBD). Among several currently used therapies are azulphidine, steroids and in more serious cases Azathioprine, 6-mercaptopurine and methotrexate are appropriate. When steroids fail, cyclosporine A may utilized. IBD's involve both local and systemic alteration of the immune system. In recent years several studies were carried out using peripheral immune cells as well colonic biopsies to examine the direct effect of possible therapeutic agents on the condition. Data indicates that the milieu of peripheral PBMC is altered and agents that were found to be disease modifiers by in situ testing were considered suitable for clinical application.

It has been observed that PIF has immune modulatory properties and such peptides are useful in the prevention and/or treatment of various immune-mediated diseases, including, but not limited to, autoimmune disorders. Compositions and methods for treating and/or preventing immune-mediated disorders are provided herein.

SUMMARY

Embodiments of the present invention provide compounds having immune-modulating and/or anti-inflammatory activity, wherein compounds of the invention include peptides and peptidomimetics. The invention further provides methods of using immune-modulating and/or anti-inflammatory compounds of the invention.

Embodiments of the present invention relate to biological effects induced in vitro and/or in vivo by pre-implantation factor, (PIF), peptides, peptidomimetics, and compounds derived from pre-implantation embryos that harbors in part, is identical to, or is homologous to the amino acid sequence of PIF peptides or to the scrambled amino acid sequence of PIF peptides. The invention also relates to the development of antibodies to quantitatively detect PIFs peptides in biological fluids.

The present invention also relates to the use of PIF antibodies for immunocytochemical and Western blot to identify PIF related proteins in pregnant tissues, fetus and placenta. This allows identifying pregnancy pathologies like premature labor and growth restriction as non-limiting examples. The PIF antibodies used as affinity column can identify associated functional proteins in pregnant tissues as seen by identification of 10 distinct proteins in the term placenta, several of them novel for that tissue. In such embodiment, other biomarkers can be identified that may be modified by pregnancy disorders. Identification of these proteins allows the examination of the genes that are associated with these proteins highly relevant for blastocyst development. These proteins using mass spectrometry or antibodies can also aid together with PIF peptides to determine embryo viability following in vitro fertilization thereby increasing the chances for pregnancy following transfer.

Further embodiments of the present invention provide methods for treating a disease characterized by an immune disorder or inflammatory response by administering an amount of a PIF peptide or peptidomimetic sufficient to treat, inhibit, or ameliorate the disease. Such compounds are useful for treating diseases characterized by an immune disorder or inflammatory response diseases, e.g., inflammation, arthritis, auto-immune diseases, collagen diseases, or allergy. For example, these compounds can be used to treat subjects, including mammals such as humans, having or at risk of having inflammation, arthritis, auto-immune diseases, collagen diseases, or allergy.

Embodiments of the present invention relate to biological effects induced in vitro and/or in vivo by pre-implantation factor (PIF) peptides, peptidomimetics, and compounds derived from pre-implantation embryos that harbors in part, is identical to, or is homologous to the amino acid sequence of PIF peptides or to the scrambled amino acid sequence of PIF peptides. In particular, the present invention relates to use of PIF peptides or peptidomimetics to effect changes on the immune system of a patient. More specifically, the addition of PIF peptides creates specific changes both in cellular immunity, as well as in a patient's secreted cytokine profile.

DESCRIPTION OF THE DRAWINGS

In part, other aspects, features, benefits and advantages of the embodiments of the present invention will be apparent with regard to the following description, appended claims and accompanying drawings where:

DETAILED DESCRIPTION

Figure 1:
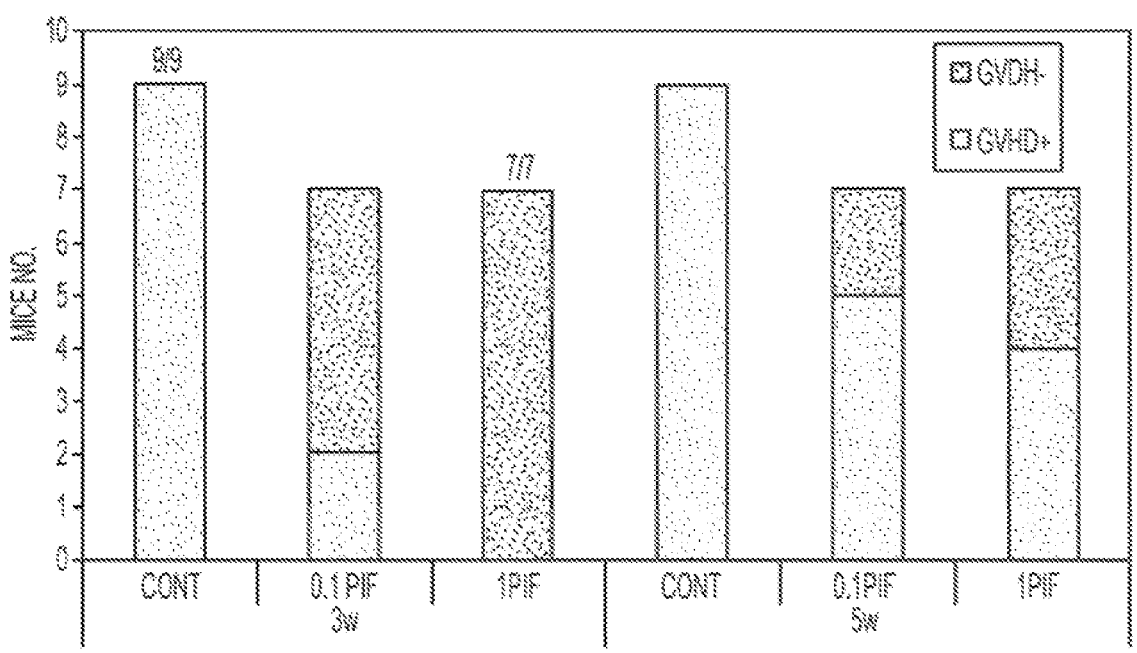
FIG. 1. PIF prevents GVHD development following high burden BMT. The number of GVHD+ and GVHD− mice at three and five weeks after BMT were evaluated. The differences between control and both 0.1 and 1 mg/kg/day PIF administered for two weeks PIF group and tested one week later were significant. Also, the 1 mg/kg/day PIF-treated group using an Alzet® pump at five weeks after BMT provided significant protection, $\chi^2$: P≤0.001, P≤0.01 and P≤0.05, respectively.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to "a cell" is a reference to one or more cells and equivalents thereof known to those skilled in the art, and so forth.

Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with PIF, can include, but is not limited to, providing PIF peptide into or onto the target tissue; providing PIF peptide systemically to a patient by, e.g., intravenous injection whereby the therapeutic reaches the target; providing PIF peptide in the form of the encoding sequence thereof to the target (e.g., by so-called gene-therapy techniques). "Administering" a composition may be accomplished by parenteral, oral or topical administration.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal without the production of undesirable physiological effects such as nausea, dizziness, rash, or gastric upset. In a preferred embodiment, the therapeutic composition is not immunogenic when administered to a subject for therapeutic purposes.

As used herein, the term "therapeutic" means an agent utilized to treat, combat, ameliorate, prevent or improve an unwanted condition or disease of a subject. In part, embodiments of the present invention are directed to treating, ameloriating, preventing or improving inflammation and/or an immune-mediate disorder, including auto-immune diseases.

A "therapeutically effective amount" or "effective amount" of a composition is a predetermined amount calculated to achieve the desired effect, i.e., to effectively inhibit or reduce inflammation and/or an immune-mediated disease. Effective amounts of compounds of the present invention can objectively or subjectively reduce or decrease the severity or frequency of symptoms associated with inflammation and/or immune-mediated disorders. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from about 0.01 mg/kg to about 10 mg/kg, more preferably about 0.1 mg/kg to about 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

"Disease" or "disorder" refers to an impairment of the normal function of an organism. As used herein, a disease may be characterized by, e.g., an immune disorder or an inflammatory response or a combination of these conditions.

"Immune-modulating" refers to the ability of a compound of the present invention to alter (modulate) one or more aspects of the immune system. The immune system functions to protect the organism from infection and from foreign antigens by cellular and humoral mechanisms involving lymphocytes, macrophages, and other antigen-presenting cells that regulate each other by means of multiple cell-cell interactions and by elaborating soluble factors, including lymphokines and antibodies, that have autocrine, paracrine, and endocrine effects on immune cells.

"Immune disorder" refers to abnormal functioning of the immune system. Immune disorders can be caused by deficient immune responses (e.g., HIV, AIDS) or overactive immune responses (e.g., allergy, auto-immune disorders). Immune disorders can result in the uncontrolled proliferation of immune cells, uncontrolled response to foreign antigens or organisms leading to allergic or inflammatory diseases, aberrant immune responses directed against host cells leading to auto-immune organ damage and dysfunction, or generalized suppression of the immune response leading to severe and recurrent infections. Immune disorder refers to disorders of the innate immune system (innate immunity) and the adaptive immune system (adaptive immunity) Innate immunity refers to an early system of defense that depends on invariant receptors recognizing common features of pathogens. The innate immune system provides barriers and mechanisms to inhibit foreign substances, in particular through the action of macrophages and neutrophils. The inflammatory response is considered part of innate immunity. The innate immune system is involved in initiating adaptive immune responses and removing pathogens that have been targeted by an adaptive immune response. However, innate immunity can be evaded or overcome by many pathogens, and does not lead to immunological memory. Adaptive immunity refers to the ability to recognize pathogens specifically and to provide enhanced protection against reinfection due to immunological memory based on clonal selection of lymphocytes bearing antigen-specific receptors. A process of random recombination of variable receptor gene segments and the pairing of different variable chains generates a population of lymphocytes, each bearing a distinct receptor, forming a repertoire of receptors that can recognize virtually any antigen. If the receptor on a lymphocyte is specific for a ubiquitous self antigen, the cell is normally eliminated by encountering the antigen early in its development. Adaptive immunity is normally initiated when an innate immune response fails to eliminate a new infection, and antigen and activated antigen-presenting cells are delivered to draining lymphoid tissues. When a recirculating lymphocyte encounters its specific foreign antigen in peripheral lymphoid tissues, it is induced to proliferate and its progeny then differentiate into effector cells that can eliminate the infectious agent. A subset of these proliferating lymphocytes differentiate into memory cells, capable of responding rapidly to the same pathogen if it is encountered again.

Immune disorders caused by an impaired or immunocompromised immune system can produce a deficient immune response that leaves the body vulnerable to various viral, bacterial, or fungal opportunistic infections. Causes of immune deficiency can include various illnesses such as viruses, chronic illness, or immune system illnesses. Diseases characterized by an impaired immune system include, but are not limited to, HIV/AIDS and severe combined immunodeficiency syndrome (SCIDS).

Immune disorders caused by an excessive response by the immune system. This excessive response can be an excessive response to one or more antigens on a pathogen, or to an antigen that would normally be ignored by the immune system. Diseases characterized by an overactive immune system include, but are not limited to, arthritis, allergy, asthma, pollinosis, atopy, and auto-immune diseases.

"Arthritis" refers to inflammation of the joints that can be caused, inter alia, by wear and tear on joints, or auto-immune attack on connective tissues, or exposure to an allergen, e.g., as in adjuvant-induced arthritis. Arthritis is often associated with, or initiated by, deposition of antibody-antigen complexes in joint membranes and activation of an inflammatory response. Sometimes the immune response is initiated by cells rather than antibodies, where the cells can produce a deposit in the joint membrane.

"Allergy" refers to an immune reaction to a normally innocuous environmental antigen (allergen), resulting from the interaction of the antigen with antibodies or primed T cells generated by prior exposure to the same antigen. Allergy is characterized by immune and inflammatory aspects, as the allergic reaction is triggered by binding of the antigen to antigen-specific IgE antibodies bound to a high-affinity IgE receptor on mast cells, which leads to antigen-induced cross-linking of IgE on mast cell surfaces, causing the release of large amounts of inflammatory mediators such as histamine. Later events in the allergic response involve leukotrienes, cytokines, and chemokines, which recruit and activate eosinophils and basophils. The late phase of this response can evolve into chronic inflammation, characterized by the presence of effector T cells and eosinophils, which is most clearly seen in chronic allergic asthma.

"Asthma" refers to a chronic inflammatory disorder affecting the bronchial tubes, usually triggered or aggravated by allergens or contaminants. Asthma is characterized by constriction of the bronchial tubes, producing symptoms including, but not limited to, cough, shortness of breath, wheezing, excess production of mucus, and chest constriction "Atopy" refers to the tendency to develop so-called "classic" allergic diseases such as atopic dermatitis, allergic rhinitis (hay fever), and asthma, and is associated with a capacity to produce an immunoglobulin E (IgE) response to common allergens. Atopy is often characterized by skin allergies including but not limited to eczema, urticaria, and atopic dermatitis. Atopy can be caused or aggravated by inhaled allergens, food allergens, and skin contact with allergens, but an atopic allergic reaction may occur in areas of the body other than where contact with the allergan occurred. A strong genetic (inherited) component of atopy is suggested by the observation that the majority of atopic dermatitis patients have at least one relative who suffers from eczema, asthma, or hay fever.

"Pollinosis," "hay fever," or "allergic rhinitis," are terms that refer to an allergy characterized by sneezing, itchy and watery eyes, a runny nose and a burning sensation of the palate and throat. Often seasonal, pollinosis is usually caused by allergies to airborne substances such as pollen, and the disease can sometimes be aggravated in an individual by exposure to other allergens to which the individual is allergic.

"Auto-immune" refers to an adaptive immune response directed at self antigens. "Auto-immune disease" refers to a condition wherein the immune system reacts to a "self" antigen that it would normally ignore, leading to destruction of normal body tissues. Auto-immune disorders are considered to be caused, at least in part, by a hypersensitivity reaction similar to allergies, because in both cases the immune system reacts to a substance that it normally would ignore. Auto-immune disorders include, but are not limited to, Hashimoto's thyroiditis, pernicious anemia, Addison's disease, type I (insulin dependent) diabetes, rheumatoid arthritis, systemic lupus erythematosus, dermatomyositis, Sjogren's syndrome, lupus erythematosus, multiple sclerosis, myasthenia gravis, Reiter's syndrome, and Grave's disease, alopecia areata, anklosing spondylitis, antiphospholipid syndrome, auto-immune hemolytic anemia, auto-immune hepatitis, auto-immune inner ear disease, auto-immune lymphoproliferative syndrome (ALPS), auto-immune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, CREST syndrome, Crohn's disease, Dego's disease, dermatomyositis, dermatomyositis, discoid lupus, essential mixed cryoglobulinemia, fibromyalgia-fibromyositis, Guillain-Barre syndrome, idiopathic pulmonary fibrosis, idiopathic thrombocytopenia purpura (ITP), IgA nephropathy, juvenile arthritis, Meniere's disease, mixed connective tissue disease, pemphigus vulgaris, polyarteritis nodosa, polychondritis, polyglancular syndromes, polymyalgia rheumatica, polymyositis, primary agammaglobulinemia, primary biliary cirrhosis, psoriasis, Raynaud's phenomenon, rheumatic fever, sarcoidosis, scleroderma, stiff-man syndrome, Takayasu arteritis, temporal arteritis/giant cell arteritis, ulcerative colitis, uveitis, vasculitis, vitiligo, and Wegener's granulomatosis.

"Collagen disease" or "connective tissue disease" refers to a chronic inflammatory auto-immune disorder in which autoantibodies attack collagen found throughout the body. Connective tissues are composed of two major structural protein molecules, collagen and elastin; in collagen disease, autoantibodies directed against collagen will damage both collagen and elastin due to the resulting inflammation. Collagen diseases include, but are not limited to, lupus erythematosus, Sjogren's syndrome, scleroderma, dermatomyositis, and polyarteritis nodosa. Rheumatoid-collagen disease refers to a disorder affecting the connective tissue, with "rheumatic" symptoms including muscle stiffness, soreness and pain in the joints and associated structures.

"Inflammatory response" or "inflammation" is a general term for the local accumulation of fluid, plasma proteins, and white blood cells initiated by physical injury, infection, or a local immune response. Inflammation is an aspect of many diseases and disorders, including but not limited to diseases related to immune disorders, viral infection, arthritis, auto-immune diseases, collagen diseases, allergy, asthma, pollinosis, and atopy. Inflammation is characterized by rubor (redness), dolor (pain), calor (heat) and tumor (swelling), reflecting changes in local blood vessels leading to increased local blood flow which causes heat and redness, migration of leukocytes into surrounding tissues (extravasation), and the exit of fluid and proteins from the blood and their local accumulation in the inflamed tissue, which results in swelling and pain, as well as the accumulation of plasma proteins that aid in host defense. These changes are initiated by cytokines produced by activated macrophages. Inflammation is often accompanied by loss of function due to replacement of parenchymal tissue with damaged tissue (e.g., in damaged myocardium), reflexive disuse due to pain, and mechanical constraints on function, e.g., when a joint swells during acute inflammation, or when scar tissue bridging an inflamed joint contracts as it matures into a chronic inflammatory lesion.

"Anti-inflammatory" refers to the ability of a compound of the present invention to prevent or reduce the inflammatory response, or to soothe inflammation by reducing the symptoms of inflammation such as redness, pain, heat, or swelling.

Inflammatory responses can be triggered by injury, for example injury to skin, muscle, tendons, or nerves. Inflammatory responses can also be triggered as part of an immune response. Inflammatory responses can also be triggered by infection, where pathogen recognition and tissue damage can initiate an inflammatory response at the site of infection. Generally, infectious agents induce inflammatory responses by activating innate immunity. Inflammation combats infection by delivering additional effector molecules and cells to augment the killing of invading microorganisms by the frontline macrophages, by providing a physical barrier preventing the spread of infection, and by promoting repair of injured tissue. "Inflammatory disorder" is sometimes used to refer to chronic inflammation due to any cause.

Diseases characterized by inflammation of the skin, often characterized by skin rashes, include but are not limited to dermatitis, atopic dermatitis (eczema, atopy), contact dermatitis, dermatitis herpetiformis, generalized exfoliative dermatitis, seborrheic dermatitis, drug rashes, erythema multiforme, erythema nodosum, granuloma annulare, poison ivy, poison oak, toxic epidermal necrolysis and roseacae.

Inflammation triggered by various kinds of injuries to muscles, tendons or nerves caused by repetitive movement of a part of the body are generally referred to as repetitive strain injury (RSI). Diseases characterized by inflammation triggered by RSI include, but are not limited to, bursitis, carpal tunnel syndrome, Dupuytren's contracture, epicondylitis (e.g. "tennis elbow"), "ganglion" (inflammation in a cyst that has formed in a tendon sheath, usually occurring on the wrist) rotator cuff syndrome, tendinitis (e.g., inflammation of the Achilles tendon), tenosynovitis, and "trigger finger" (inflammation of the tendon sheaths of fingers or thumb accompanied by tendon swelling).

It is understood that the terms "immune disorder" and "inflammatory response" are not exclusive. It is understood that many immune disorders include acute (short term) or chronic (long term) inflammation. It is also understood that inflammation can have immune aspects and non-immune aspects. The role(s) of immune and nonimmune cells in a particular inflammatory response may vary with the type of inflammatory response, and may vary during the course of an inflammatory response. Immune aspects of inflammation and diseases related to inflammation can involve both innate and adaptive immunity. Certain diseases related to inflammation represent an interplay of immune and nonimmune cell interactions, for example intestinal inflammation (Fiocchi et al., 1997, Am J Physiol Gastrointest Liver Physiol 273: G769-G775), pneumonia (lung inflammation), or glomerulonephritis.

It is further understood that many diseases are characterized by both an immune disorder and an inflammatory response, such that the use of discrete terms "immune disorder" or "inflammatory response" is not intended to limit the scope of use or activity of the compounds of the present invention with respect to treating a particular disease. For example, arthritis is considered an immune disorder characterized by inflammation of joints, but arthritis is likewise considered an inflammatory disorder characterized by immune attack on joint tissues. Thus, the observation that a compound of the invention reduces the inflammation seen in an animal model of arthritis, does not limit the observed activity of the compound to anti-inflammatory activity. In a disease having both immune and inflammatory aspects, merely measuring the effects of a compound of the present invention on inflammation does not exclude the possibility that the compound may also have immune-modulating activity in the same disease. Likewise, in a disease having both immune and inflammatory aspects, merely measuring the effects of a compound of the present invention on immune responses does not exclude the possibility that the compound may also have anti-inflammatory activity in the same disease.

As used herein, the terms "peptide," "polypeptide" and "protein" are used interchangeably and refer to two or more amino acids covalently linked by an amide bond or non-amide equivalent. The peptides of the invention can be of any length. For example, the peptides can have from about two to about 100 or more residues, such as, 5 to 12, 12 to 15, 15 to 18, 18 to 25, 25 to 50, 50 to 75, 75 to 100, or more in length. Preferably, peptides are from about 2 to about 18 residues. The peptides of the invention include l- and d-isomers, and combinations of l- and d-isomers. The peptides can include modifications typically associated with post-translational processing of proteins, for example, cyclization (e.g., disulfide or amide bond), phosphorylation, glycosylation, carboxylation, ubiquitination, myristylation, or lipidation.

Peptides disclosed herein further include compounds having amino acid structural and functional analogues, for example, peptidomimetics having synthetic or non-natural amino acids or amino acid analogues, so long as the mimetic has one or more functions or activities of compounds of the invention. The compounds of the invention therefore include "mimetic" and "peptidomimetic" forms.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

In one embodiment, the PIF peptides of the invention are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7 membered alkyl, amide, amide lower alkyl, amide di (lower alkyl), lower alkoxy, hydroxy, carboxy and the lower ester derivatives thereof, and with 4-, 5-, 6-, to 7 membered heterocyclics. For example, proline analogs can be made in which the ring size of the proline residue is changed from 5 members to 4, 6, or 7 members. Cyclic groups can be saturated or unsaturated, and if unsaturated, can be aromatic or nonaromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, Ann. Rep. Med. Chem. 24, 243-252, 1989). Certain peptidomimetic compounds are based upon the amino acid sequence of the peptides of the invention. Often, peptidomimetic compounds are synthetic compounds having a three-dimensional structure (i.e. a "peptide motif") based upon the three-dimensional structure of a selected peptide. The peptide motif provides the peptidomimetic compound with the desired biological activity, i.e., binding to PIF receptors, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, Curr. Op. Chem. Biol. 2, 441-452, 1998; Hruby et al., Curr. Op. Chem. Biol. 1, 114-119, 1997; Hruby & Balse, Curr. Med. Chem. 9, 945-970, 2000). One class of peptidomimetics a backbone that is partially or completely non-peptide, but mimics the peptide backbone atom-for atom and comprises side groups that likewise mimic the functionality of the side groups of the native amino acid residues. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

The PIF assay, as disclosed in U.S. Pat. No. 5,646,003 to Barnea et al., entitled "Preimplantation Factor" issued Jul. 9, 1997, and in U.S. Pat. No. 5,981,198 to Barnea et al., entitled "Preimplantation Factor" granted Nov. 9, 1999, the disclosures of which are incorporated herein by reference in their entirety, may be used to measure the response of the immune system to pregnancy specific preimplantation factors. Studies employing the PIF assay for culture media of human or mouse embryos that were grown, show that PIFs were able to increase the in-vitro formation of rosettes between donor lymphocytes and platelets in the presence of monoclonal anti-CD2 (type T11-1). Lymphocyte-platelet rosettes result from the interaction of the T cell surface protein CD2 with its ligand CD58 expressed on the platelet membrane. Anti-CD2, by binding to the CD2 antigen on the T cells, inhibits their interaction with platelets. However, the embryo-derived factor(s), PIFs, present in the culture medium or pregnant peripheral sera appears to counteract this inhibition. The PIF activity was already apparent in the viable two-cell stage embryo. Thus both of those compounds properties are very likely to be similar. This observation strongly suggests that there are several putative compounds that may be very potent, and create an environment that is favorable for pregnancy.

Using this assay, it has been determined that the presence of PIF activity in maternal serum within four days after embryo transfer indicates a >70% chance of successful pregnancy outcome. In contrast, absence of PIF activity indicated that pregnancy would not develop in 97% of cases. PIF is detectable 5-6 days after intrauterine insemination and is absent in non-pregnant serum and in culture media of non-viable embryos, present in the sera of various mammals including horse, cow, pig and humans. Without wishing to be bound by theory, the PIF assay results indicate that if the embryo is able to secrete these immunomodulatory PIF compounds, it is capable of implanting and achieving a good pregnancy outcome. The importance of PIF as a marker of a good quality pregnancy is further illustrated by the fact that if a pregnancy ends in miscarriage, the PIF activity progressively declines until it reaches non-detectable levels. In contrast, in the case of a poor quality pregnancy, Human Chronic Gonadotropin (hCG) levels do not change significantly for the next 3 weeks until the miscarriage is clinically evident.

PIF activity is found in several mammalian species, including humans, horse, cow, pig, and mouse and sheep. Human immune cells used for the PIF assay (homologous lymphocytes and platelets) interacted well with the human sera, as well as with sera from different species and embryo culture media. This cross-species interaction indicates that similar compounds are involved in the different species. PIF activity is due to the presence of similar low molecular weight peptides, both in mouse embryo culture media and in pregnant porcine serum. A PIF assay was used as a test to identify and characterize the PIF related compounds within a conditioned mouse embryo culture media. Using a multi-step chromatographic technique, coupled with the PIF bioassay, a group of a putative PIF embryo derived peptides with 9-18 amino acids in length were identified and sequenced. These sequences are disclosed in PCT/US02/20599 to Barnea et al., entitled "New Assays for Preimplantation Factor and Preimplantation Peptides," filed Jun. 28, 2002, the contents of which are incorporated herein by reference in their entirety. Based on the sequences derived, synthetic peptides were generated.

The first natural PIF compound identified, termed nPIF-1$_{(15)}$ (SEQ ID NO:1), is a 15 amino acid peptide. A synthetic version of this peptide, BPIF-1$_{(15)}$ (SEQ ID NO:13), showed activity that was similar to the native peptide, nPIF-1$_{(15)}$ (SEQ ID NO:1). This peptide is homologous to a small region of the Circumsporozoite protein, a malaria parasite. The second PIF peptide, nPIF-2$_{(13)}$ (SEQ ID NO:7), includes 13 amino acids and shares homology with a short portion of a large protein named thyroid and retinoic acid transcription co-repressor, which is identified as a receptor-interacting factor, (SMRT); the synthetic version is sPIF-2 (SEQ ID NO:14). The third distinct peptide, nPIF-3$_{(18)}$ (SEQ ID NO:10), consists of 18 amino acids and matches a small portion of reverse transcriptase; the synthetic version of this peptide BPIF-3$_{(18)}$ is (SEQ ID NO:15). nPIF-4$_{(9)}$ (SEQ ID NO:12) shares homology with a small portion of reverse transcriptase.

A list of PIF peptides, both natural and synthetic, are provided below in Table 1. Antibodies to various PIF peptides and scrambled PIF peptides are also provided.

TABLE 1

PIF Peptides

| (SEQ ID NO) | Peptide | Amino Acid Sequence |
|---|---|---|
| SEQ ID NO: 1<br>isolated native, matches region of<br>Circumsporozoite protein (Malaria) | nPIF-1$_{15}$ | MVRIKPGSANKPSDD |
| SEQ ID NO: 2<br>isolated native, matches region of<br>Circumsporozoite protein (Malaria) | nPIF-1$_{(15\text{-}alter)}$ | MVRIKYGSYNNKPSD |
| SEQ ID NO: 3<br>isolated native, matches region of<br>Circumsporozoite protein (Malaria) | nPIF-1$_{(13)}$ | MVRIKPGSANKPS |
| SEQ ID NO: 4<br>isolated native, matches region of<br>Circumsporozoite protein (Malaria) | nPIF-1$_{(9)}$ | MVRIKPGSA |
| SEQ ID NO: 5<br>synthetic, scrambled amino acid sequence<br>from region of Circumsporozoite protein<br>Malaria | scrPIF-1$_{15}$ | GRVDPSNKSMPKDIA |
| SEQ ID NO: 6<br>isolated native, matches region of human<br>retinoid and thyroid hormone receptor-SMRT | nPIF-2$_{(10)}$ | SQAVQEHAST |
| SEQ ID NO: 7<br>isolated native, matches region of human<br>retinoid and thyroid hormone receptor (SMRT) | nPIF-2$_{(13)}$ | SQAVQEHASTNMG |
| SEQ ID NO: 8<br>synthetic, scrambled amino acid sequence<br>from region of human retinoid and thyroid<br>hormone receptor SMRT | scrPIF-2$_{(13)}$ | EVAQHSQASTMNG |

TABLE 1 -continued

PIF Peptides

| (SEQ ID NO) | Peptide | Amino Acid Sequence |
|---|---|---|
| SEQ ID NO: 9 | scrPIF-2 $_{(14)}$ | GQASSAQMNSTGVH |
| SEQ ID NO: 10<br>isolated native, matches region of Rev Trans | nPIF-3 $_{(18)}$ | SGIVIYQYMDDRYVGSDL |
| SEQ ID NO: 11<br>synthetic, scrambled amino acid sequence<br>from region of Circumsporozoite protein<br>Malaria | Neg control<br>for<br>negPIF-1 $_{(15)}$ | GMRELQRSANK |
| SEQ ID NO: 12<br>isolated native, matches region of Rev Trans | nPIF-4 $_{(9)}$ | VIIIAQYMD |
| antibody of native isolated nPIF-1 $_{15}$ | AbPIF-1 $_{(15)}$ | |
| (SEQ ID NO: 13)<br>synthetic, amino acid sequence from region<br>of Circumsporozoite protein Malaria | sPIF-1 $_{(15)}$ | MVRIKPGSANKPSDD |
| (SEQ ID NO: 14)<br>synthetic, amino acid sequence from of human<br>retinoid and thyroid hormone receptor SMRT | sPIF-2 $_{(13)}$ | SQAVQEHASTNMG |
| (SEQ ID NO: 15)<br>synthetic, amino acid sequence from region<br>of Circumsporozoite protein Malaria | sPIF-3 $_{(18)}$ | SGIVIYQYMDDRYVGSDL |
| (SEQ ID NO: 16)<br>synthetic, amino acid sequence from region<br>of Circumsporozoite protein Malaria | sPIF-1 $_{(9)}$ | MVRIKPGSA |
| antibody of native isolated nPIF-2 $_{(13)}$ | AbPIF-2 $_{(13)}$ | |
| antibody of native isolated nPIF-3 $_{(18)}$ | AbPIF-3 $_{(18)}$ | |
| (SEQ ID NO: 17)<br>synthetic | sPIF-4 $_{(9)}$ | VIIIAQYMD |
| SEQ ID NO: 18<br>synthetic | sPIF-1 $_{(5)}$ | MVRIK |
| SEQ ID NO: 19<br>synthetic | sPIF-1 $_{(4)}$ | PGSA | n = native,
s = synthetic,
scr = scrambled,
same AA,
( ) = number of AA,
Ab = antibody In another embodiment, a method of detecting a PIF peptide is provided. The PIF peptide may include, for example, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17. In a further embodiment, a method of detecting a PIF peptide which includes a fragment of nPIF-1 $_{15}$, nPIF-2 $_{13}$, nPIF-3 $_{18}$ or nPIF-4 $_9$.

PIF peptides and peptidemimetics of the present invention may be coupled to produce labeled peptides, for example but not limited to FITC, biotin, rhodamine, radioactive labels, fluorescent nanocrystals, and other labels known to those skilled in the art, that may be used to identify PIF receptor sites present on immune cells, endometrium, on the embryo itself, as well as elsewhere within the body where PIF peptides specifically bind.

Embodiments of the present invention may be used to identify and clone the genes that are responsible for PIF peptides expression. cDNA library is prepared from human placenta (Invitrogen) that have libraries of 1-2.5 kb size inserts which represent even the rarest sequences. Oligonucleotides are generated based on the peptides sequences and are probed against the cDNA library using plate screening procedures. The PIF peptide presence in the placenta was adding previously documented using immunohistochemical techniques by labeled PIF-1 antibody. The species of PIF peptides present in the placenta are confirmed with affinity purified and labeled PIF-1, PIF-2, and PIF-3 antibodies using a Western blot. The present invention may be used to generate specific antibodies polyclonal and monoclonal for assay development to measure PIF levels and activity in biologic fluids and tissues such as but not limited to serum, blood, urine, milk, and saliva as well as embryo culture media, gestational tissue, and fetal tissue.

Another embodiment of the present invention provides for making polyclonal or monoclonal antibodies that were raised against PIF. In one non-limiting embodiment, polyclonal or monoclonal antibodies may be raised against PIF in mice and rabbits. In another embodiment, antibodies to PIF may be created by providing a hybridoma cell that produces a monoclonal antibody specific for a PIF peptide and culturing the cell.

Such antibodies provide a method for determining the presence of PIF levels in samples by using but not limited to ELISA, EIA, lateral flow assay, microfluidics or mass spectometry. Such a method and antibodies may allow precise measurements of PIF levels in fluids such as but not limited to maternal blood, urine, saliva, milk, and embryo culture media and gestational tissues. The method is applicable for all PIF peptides and may be used to provide an early diagnostic method that reflects pregnancy and its viability in various patients starting at the pre-implantation period. The patients may include women, to monitor results of infertility therapy and pregnancy well being, as well as other mammals, including farm and non-farm animals, and non-mammals. In the embryo culture media the ELISA assay using such antibodies provides a method for assessing the presence of PIF peptides to assess embryo viability before transfer. Various aspects of the present invention will be illustrated with reference to the following non-limiting examples.

In one embodiment of the present invention, a PIF peptide is provided. Such PIF peptides may be useful for treating or ameliorating immune-mediated disorders, such as autoimmune diseases.

In another embodiment, a pharmaceutical composition comprising a PIF peptide is provided. In preferred embodiments, the pharmaceutical composition comprises an effective amount of a PIF peptide.

In another embodiment, a method of treating or preventing immune-mediated disorders is provided. In a preferred embodiment, the method comprises administering an effective amount of a PIF peptide to a subject in need thereof. The methods are particularly useful in treating or preventing immune-mediated disorders, including, but not limited to, graft-versus-host disease, type 1 diabetes, multiple sclerosis, ulcerative colitis, Crohn's disease, rheumatoid arthritis and the like.

In a further embodiment, a method for treating or preventing immune-mediated disorders comprising administering an effective amount of a PIF peptide in combination with one or more immunotherapeutic drugs to a subject in need thereof is provided. Such a combination may enhance the effectiveness of the treatment of either component alone, or may provide less side effects and/or enable a lower dose of either component.

The present data demonstrate that short-term exposure to PIF-1 at low doses is associated with a long-term protection against development of autoimmune disorders of disparate origin. While not wishing to be bound by theory, based on the currently understood aspects of PIF-1's mechanism of action, the peptide appears to act independently of the type of pathophysiological features of the autoimmune disease examined addressing them in an etiology-independent manner. This agrees with the properties of PIF-1 following examination of its effects on PBMC. PIF-1 was found to have widespread modulatory effects on cellular immunology, as well as on cytokine production and secretion acting through specific inducible receptors present on subtypes of PBMC. PIF-1 appears to affect disparate aspects of immunity since it responds to various mitogen challenge, PHA, CD3MAb, CD3MAb/CD28MAb, and MLR. PIF-1 exposure blocks activated, but not basal, PBMC proliferation. In addition while there was some bias towards $T_H2$, PIF-1 caused an increase in both $T_H1$ and $T_H2$ cytokines following mitogen exposure. This may indicate that PIF-1 helps to maintain the balance between the two immune modalities, not allowing either extreme inflammation or immune suppression. By blocking activated, but not basal, immunity the ability to respond to an immunogenic challenge such as pathogen exposure, and/or maternal rejection is well maintained. This may explain the significant efficacy observed in the current mouse studies. Overall, PIF-1's mechanism of action is distinct from other currently used immune suppressive agents.

The three autoimmune models studied are quite distinct: BMT replicates exposure of the model organism to foreign immune cells as would be the case in GVHD; NOD replicates Type 1 diabetes induced by a specific attack on the pancreas by transplanted foreign T cells; and EAE models MS by stimulating a bacterial toxin and protein immunogen attack on the nervous tissue of the brain. However, all of the models are characterized by an induced immune response against the host organism and, consequently, to the autoimmune-induced destruction of vital organs and, ultimately, death. PIF-1 appears to successfully neutralize the initiation of this cascade irrespective of the initiating insult. This can be analogized to pregnancy, in which the embryo is tolerated by the mother, but the mother remains able to respond adequately to pathogens. Pregnancy may also leave the mother less susceptible to autoimmunity and malignancy, to some degree. Therefore, recreating an environment where select cells are tolerated while pathogens are attacked in a non-pregnancy setting may be the central mechanism of PIF-1's action in autoimmune model systems.

In all three models, efficacy was obtained in low doses, 0.1-1 mg/kg/day. By contrast, somewhat lower efficacy is observed at higher dosing in two models (NOD 2.73 mg/kg/day and BMT 5 mg/kg/day). This agrees with in vitro data where maximal PIF-1 efficacy was found at 1-50 nM concentrations, while higher doses were either less effective or not effective at all. This further suggests a receptor-dependent mechanism of action that is mostly responsive at a narrow range of concentrations and otherwise may be down-regulated when concentrations are raised beyond optimal levels. These observations strongly indicate that PIF exerts this biphasic effect through physiological and not pharmacological mechanisms.

While the mechanism for the long-term protective effect of PIF-1 as seen in these autoimmune models is not clear, and without wishing to be bound by theory, it appears that PIF-1 initiates, following mitogen exposure, a time-dependent block of proliferation and leads to a cascade of $T_H1$ and $T_H2$ cytokine secretion, some being secreted earlier while others, later. Such sequential effects may lead to a long-term modification of the immune environment.

PIF-1 appears to act through putatively novel receptors that are predominantly expressed on monocytes and macrophages. However, when stimulated by mitogens, the expression of these receptors becomes significant on T and B Cells but not NK cells. Differences in the expression pattern of PIF-1 receptors may explain the differences in the response induced by PIF-1 seen in un-stimulated and stimulated environments. In an un-stimulated environment, PIF-1 may only have a low level of activity on T and B Cells. However, activation of the immune system in response to an immune system challenge may lead to the expression of the PIF-1 receptors on T and B Cells initiating long term tolerance.

PIF-1's action appears to be independent of TCR, calcium-channels or PKC pathways, mechanisms through which most immune-suppressive agents act, and CD4+/CD25+ cells (T reg) cells that are of relevance in various autoimmune diseases. On the other hand, PIF-1's action may involve NFAT-1 suppression.

In pregnancy, embryo viability is dependent on maternal tolerance of the embryo, but there is a clear time lag between embryo expulsion by miscarriage and reduction of PIF levels in maternal circulation. In fact, PIF disappears from maternal circulation up to three weeks before maternal human chorionic gonadotropin (hCG) levels dropped and miscarriage ensues. Perhaps, a similar mechanism is involved in maintaining tolerance, or protective effects against autoimmunity long term, as is documented in the three model systems tested following cessation of therapy.

In a preliminary study, the effect of PIF-1 administration using an Alzet® pump for 7 days after mating on implantation rates in mice was examined. As expected, PIF-1 did not exert any adverse effects. Moreover, PIF-1 may have actually increased the rates of fetal survival vs. control by day 13 of pregnancy, as documented at the time of Ceasarean section. This data combined with the additional six animal trials provides a strong support for the lack of PIF-1 toxicity.

We also found that FITC-PIF-1 injected IV in mice accumulated in the spleen and was cleared from circulation into the kidney within minutes. This shows that PIF-1 specifically targets immune cells of the spleen in vivo, and has a short half-life in circulation. The long term effect of PIF administration may reflect a pharmacodynamic type of mechanism since the peptide has a short half-life, rather than a pharmacologic effect that is produced while the drug is given and is dependent on the levels of the drug in the circulation.

The observations that PIF-1 exerts long-term protection after short-term exposure in all three models tested raises the possibility that PIF-1 therapy could be used for long-term management of patients with autoimmune diseases, perhaps initially using an insulin pump that could replicate the function of an Alzet® pump followed by periodic PIF-1 administration, over a long term. Other devices capable of continuous and/or long term administration may also be useful. In addition, it may be possible to develop an increased half-life, modified peptide (such as by PEGylation) and/or to use transdermal delivery system for long term, but minimally invasive use. Finally, due to PIF-1's simple structure and small size, in which shorter versions of the peptide are similarly effective (at least in vitro), oral delivery may become possible, which could transform PIF-1 into a convenient chronic therapy.

Ultimately, a novel embryo-derived peptide, PIF, creates a tolerogenic state at low doses following short-term treatment leading to long-term protection in several distinct severe autoimmune models. This effect is exerted without apparent toxicity.

For therapeutic treatment of the specified indications, a PIF peptide may be administered as such, or can be compounded and formulated into pharmaceutical compositions in unit dosage form for parenteral, transdermal, rectal, nasal, local intravenous administration, or, preferably, oral administration. Such pharmaceutical compositions are prepared in a manner well known in the art and comprise at least one active PIF peptide associated with a pharmaceutically carrier. The term "active compound", as used throughout this specification, refers to at least one compound selected from compounds of the formulas or pharmaceutically acceptable salts thereof.

In such a composition, the active compound is known as "active ingredient." In making the compositions, the active ingredient will usually be mixed with a carrier, or diluted by a carrier, or enclosed within a carrier that may be in the form of a capsule, sachet, paper or other container. When the carrier serves as a diluent, it may be a solid, semisolid, or liquid material that acts as a vehicle, excipient of medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

The local delivery of inhibitory amounts of active compound for the treatment of immune disorders can be by a variety of techniques that administer the compound at or near the targeted site. Examples of local delivery techniques are not intended to be limiting but to be illustrative of the techniques available. Examples include local delivery catheters, site specific carriers, implants, direct injection, or direct applications, such as topical application.

Local delivery by an implant describes the surgical placement of a matrix that contains the pharmaceutical agent into the affected site. The implanted matrix releases the pharmaceutical agent by diffusion, chemical reaction, or solvent activators.

For example, in some aspects, the invention is directed to a pharmaceutical composition comprising a PIF peptide, and a pharmaceutically acceptable carrier or diluent, or an effective amount of a pharmaceutical composition comprising a PIF peptide.

The compounds of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, ocular routes, intravaginally, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular mammal or human treated, age, weight, health, types of concurrent treatment, if any, and frequency of treatments, and can be easily determined by one of skill in the art (e.g., by the clinician).

Pharmaceutical formulations containing the compounds of the present invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion subcutaneously over a predetermined period of time. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, or other compatible drugs or compounds where such combination is seen to be desirable or advantageous in achieving the desired effects of the methods described herein.

This invention and embodiments illustrating the method and materials used may be further understood by reference to the following non-limiting examples.

EXAMPLE 1

Peptide synthesis: Synthetic PIF-$1_{15}$ (MVRIKPG-SANKPSDD) was obtained by solid-phase peptide synthesis (Peptide Synthesizer, Applied Biosystems) employing Fmoc (9-fluorenylmethoxycarbonyl) chemistry. Final purification is carried out by reverse-phase HPLC and identity is verified by MALDI-TOF mass spectrometry and amino acid analysis and purified to >95%, by HPLC, and documented by mass spectrometry (Biosynthesis, Texas).

Mice: C57BL/6(H-2b) male and female and (C57BL/6xBALB/c) F1 (H-2d/b) male, five- to six-week-old mice (GVHD studies) and seven- to eight-week old SJL mice (MS studies) were purchased from Harlan (Israel), and male and female seven- to eight-week-old NOD mice were obtained from Jackson Laboratories (Maine). All mice were maintained under conditions approved by the Institutional Animal Care and Use Committee of the Hebrew University in Jerusalem in accordance with the national laws and regulations for protection of animals.

GvHD model:Recipients (C57BL/6xBALB/c) F1 mice received lethal whole-body irradiation by a single dose of 1000 rad/dose and were reconstituted with 5–8×10$^6$ C57BL/6 bone marrow (BM) cells and 10–20×10$^6$ spleen cells. BM from C57BL/6 donor mice was collected by flushing of femur, humerus and tibia into 10% FCS/PBS. BM mononuclear cells were isolated from the interface after centrifugation on a Ficoll-Hipaque gradient. Spleens were crushed through 70 µm screens into 10% FCS/PBS. BM cells plus spleen cells were inoculated intravenously into whole-body irradiated mice one-day post radiation. PIF-1 therapy (0.1-1 mg/kg/day) was administered in three separate animal trials 5-10/group vs. control by implanting under anesthesia an Alzet® pump in the dorsal subcutaneous region at the day of transplant for one to two weeks providing continuous release of PIF-1. Evaluation of GvHD model animals was carried out by examining body weight, skin lesions, animal survival, and histological examination. Animal weight was examined every three days following BM transplantation, scoring for skin manifestations of GVHD was carried out from day 12 post BMT up to four months. Skin and liver samples were fixed in 10% formalin embedded in paraffin and stained with hematoxylin and eosin and evaluated for ulcers, in the former and lymphocyte infiltration in the latter. Results were evaluated by $\chi^2$ and ANOVA.

Assay for chimerism: Mice were anesthetized and blood taken from the retro-orbital sinus of the eye. WBC (2-8×10$^5$/sample) were separated, directly stained with anti-H-2K$^b$-FITC (IgG$_{2a}$) or anti-H-2K$^d$-FITC (IgG$_{2a}$) monoclonal antibodies (mAb) (Serotec, USA), and analyzed by FACS analysis (FACStar plus, Becton Dickinson, San Jose, Calif., USA). Background binding of each H-2K-specific mAb was determined by staining with it the cells of non-relevant haplotype.

GVHD Model experiment I. Following low-burden BMT, GVHD development was examined following PIF-1 therapy (0.1-1 mg/kg/day) given for one week using an implanted Alzet® pump followed by one month observation. Of the PIF-1-treated mice, 0.1 or 1 mg/kg/day for one week, all eight mice did not develop GVHD. Four out of five controls developed GVHD grade II-III (P<0.01). Mice following BMT and short term PIF-1 treatment remained completely protected against the development of GVHD at one month after cessation of therapy. In contrast, in control mice, severe skin ulcerations and weight loss developed (mean mouse weight 21.9 g, high dose PIF-1 (N=3), 20.2 g low dose PIF-1 (N=5), and 19.5 g in controls).

Figure 2:
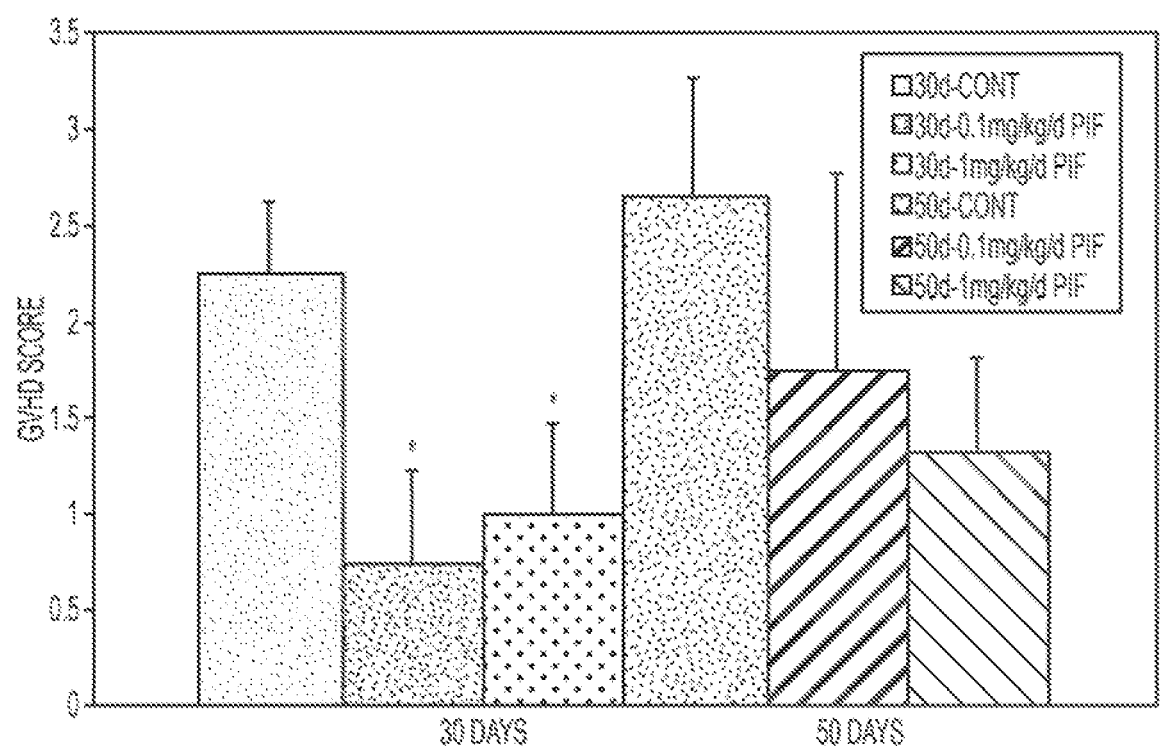
FIG. 2. PIF-treated mice with a high BMT burden that develop GVHD have a lower score at 30 days post transplant. At 30 days post-BMT, the difference between the control and the 0.1 and 1 mg/kg/day treated PIF groups using an Alzet® pump, are significant. t-test P≤0.04 and P≤0.04. At 50 days, the effect was not significant.

GVHD Model experiment II (FIG. 1). We examined whether PIF-1 could prevent GVHD development in a higher-burden BMT (double number of spleen cells transplanted than the low-burden BMT). Following exposure to PIF-1 (0.1-1 mg/kg/day) for two weeks, total protection against GVHD was obtained within three weeks with the high dose therapy 7/7 vs. 9/9 in control with GVHD. This protection remained also significant (P<0.04) at thirty days post-BMT in both treatment groups, as evaluated by the GVHD score in those which developed the disease (FIG. 2).

Figure 3:
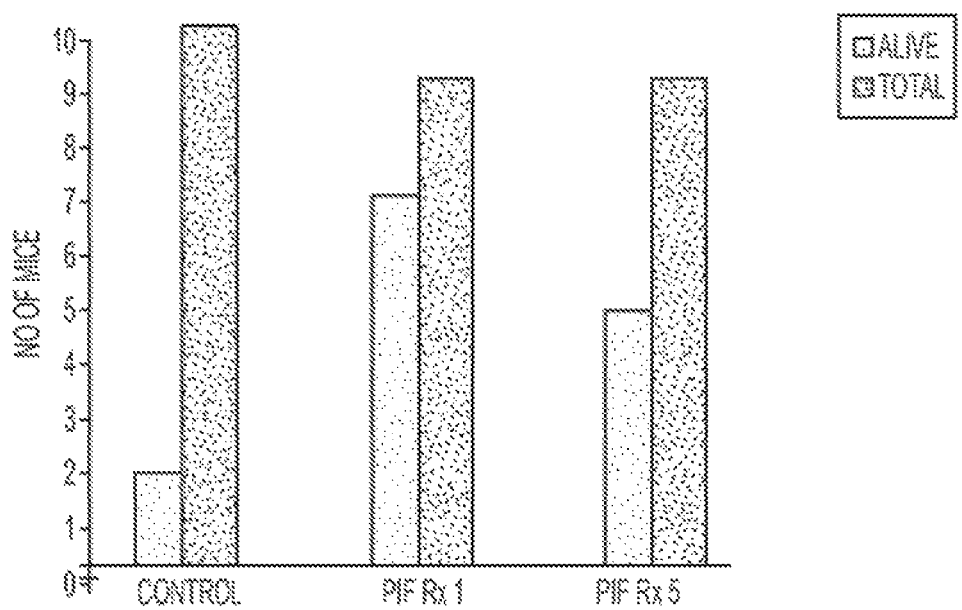
FIG. 3. Short-term PIF administration to mice with high-burden BMT is associated with long term survival. PIF 1-5 mg/kg/day for two weeks was administered using an Alzet® pump and the effect on long-term survival was compared to control. In the lower-dose PIF-treated group, 7/9 mice survived vs. control 2/10, $\chi^2$, P<0.01. The survival of the higher-dose treated group was slightly lower, 5/9.

GVHD Model experiment III (FIG. 3). We examined whether short-term treatment can lead to long term survival after cessation of therapy. Following high-burden BMT, PIF-1 1-5 mg/kg/day for two weeks was administered and mice were followed for an additional three and one-half months without therapy. PIF-1 conferred a significant protection as determined by mouse survival at the end of the observation period. Seven of nine of the PIF-1 treated mice survived compared to only two out of ten in controls (P<0.02). Higher-dose therapy was less effective, although it was still associated with a higher survival rate than controls (5/9 survived). Significant protection from weight loss was also achieved following PIF-1 1/mg/kg/day exposure vs. controls. This effect became significant after day 33 from BMT. In control mice, following BMT, GVHD-induced skin ulcerations were observed. Short-term PIF-1 therapy prevented the development of such lesions in the long term. Liver histology also documented that lymphocytic infiltrates, indicating autoimmune response, were noted in control, but not in PIF-1-treated mice one month after cessation of therapy. The degree of BMT incorporation into the recipient mice was determined. Results show that there was a quasy total incorporation of grafted bone marrow after five weeks after BMT (87.5±2.4), reflected a very high degree of chimerism.

Allo-BMT followed destruction of the host's immune system by total body radiation. Thereby the BMT recipient is highly vulnerable to immune attack by the transplanted foreign immune cells. Low dose (micromolar) PIF-1 administration totally prevented GVHD while therapy was administered. More remarkably, long-term protection after cessation of therapy was obtained, as reflected by the significant prevention of GVHD development and long-term survival for several months vs. control mice. This effect was not associated with any toxicity, as documented by mouse weight, skin appearance, and skin and liver histology. This was also documented by the significant degree of chimerism (about 90%) that developed in the peripheral PBMC within five weeks following BMT, indicating that at that time the great majority of the mice immune system was constituted of the transplanted BM.

PIF-1's long-term protective effect after cessation of therapy is particularly significant, as other BMT therapies are effective only during active administration. Furthermore, the current BMT model involved a clear mismatch between the recipient and the donor, and large quantities of cells were transplanted, while clinical settings use closely matched BM donors, which nevertheless often, up to 70% results in various degrees of GVHD.

EXAMPLE 2

Materials and methods are the same as Example 1.

DM (adoptive transfer NOD) model. Male NOD mice were irradiated (650 rad), and injected IV next day with 250 Mil spleen cells collected from female NOD diabetic mice. PIF-1 was injected in two doses 0.83 mg/kg/day (N=5) and 2.73 mg/kg/day (N=7) for 28 days using an Alzet® pump, implanted subcutaneously providing continuous release of the peptide, followed by a 40-day observation period. Animals were monitored for DM development by determining fasting glucose levels in both blood and urine. Results were evaluated using ANOVA.

Figure 4:
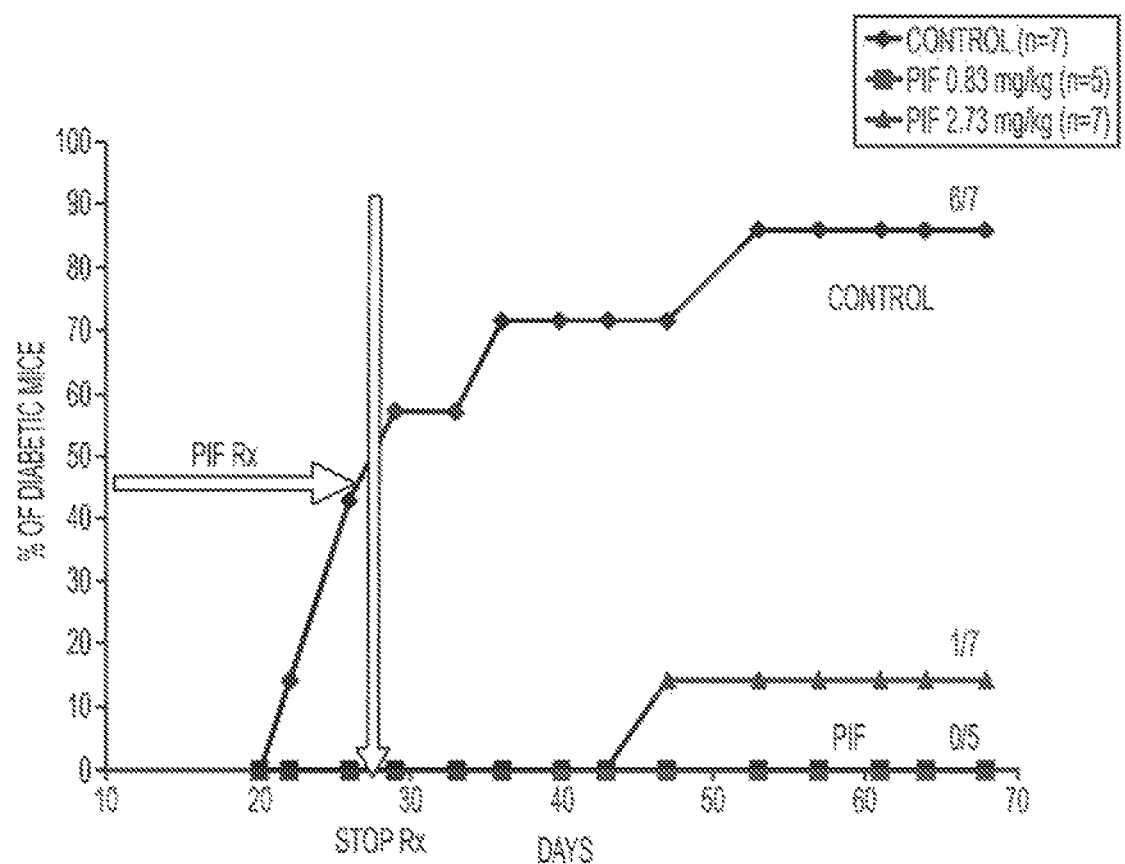
FIG. 4. PIF treatment prevents diabetes development in NOD male mice, adoptive transfer model. Male mice were injected IV with 250M spleen cells derived from diabetic female NOD mice. PIF 0.83-2.73 mg/kg/day was administered using Alzet® pump for 28 days. This was followed by a 40-day observation period. In low-dose PIF group, no mice developed DM, while in the high-dose group, one mouse became diabetic vs. 6/7 in controls, P<0.001.

NOD diabetes model. We examined the effect of PIF-1 in a different autoimmune model, NOD adoptive transfer. In this model, transfer of diabetic splenocytes from female to male mice leads progressively to the development of diabetes mellitus. Exposure to PIF-1 0.83-2.73 mg/kg/day for the first 28 days had a long-term protective effect against the destruction of pancreatic cells and the consequent high serum glucose levels. FIG. 4 shows a life table analysis of NOD mice following adoptive transfer of splenocytes from a diabetic female mouse. By 70 days, at the conclusion of the experiment, PIF-1 was totally protective in 11/12 of mice treated with PIF-1 while 6/7 in the control group has already developed diabetes. Interestingly, the only PIF-1 treated mouse that developed DM received a higher treatment dose. The development of diabetes was documented by increased serum glucose levels; in certain control animals it reached >600 mg/dl. Table 2, below, shows individual mice glucose levels after cessation of therapy.

TABLE 2

| | NOD male mice No. | Non fasting blood glucose mg/dL (day 40) | Fasting blood glucose mg/dL (day 69) |
|---|---|---|---|
| Control | 1 | >600 | 355 |
| | 2 | >600 | 377 |
| | 3 | 202 | 232 |
| | 4 | 193 | |
| | 5 | >600 | |
| | 6 | 298 | 207 |
| | 7 | 135 | 123 |
| PIF 0.83 mg/kg/day | 1 | 131 | 97 |
| | 2 | 112 | 106 |
| | 3 | 137 | 119 |
| | 4 | 132 | 109 |
| | 5 | 130 | 149 |
| PIF 2.73 mg/kg/day | 1 | 118 | 87 |
| | 2 | 126 | 108 |
| | 3 | 125 | 111 |
| | 4 | 113 | 144 |
| | 5 | 158 | 514 |
| | 6 | 123 | 103 |
| | 7 | 115 | 109 |

In the control group, most mice developed diabetes by 40 days. Additionally, histological examination demonstrated that PIF treated mice were protected against inflammation of the pancreas v. control (data not shown).

To further document PIF-1's immune-modulatory effects, we used the NOD mouse adoptive transfer model, which results in the development of diabetes (reflected by high glucose levels) due to the destruction of the recipient's pancreas by transfer of autoreactive splenocytes from a diabetic mouse that targets specifically that organ. Using this aggressive model, we documented a long-term protection against DM development using PIF-1 therapy. These results open the possibility of examining young adults that have recently developed DM in whom there has not been a total destruction of insulin-producing pancreas cells. Such an early intervention could lead to a decreased need for insulin administration, or even allow long-term oral anti-diabetic therapy. Since we found that PIF-1 targets isolated splenocytes that provides a rationale for the protective effects that were observed. In TIDM primed T cells and macrophages directly attack the pancreas which is followed by local increase in $T_H1$ cytokines (i.e., TNF, interferon-) that further amplify the auto-destructive process. PIF-1 may act on both of these aspects of autoimmunity by blocking activated immune cells proliferation activation and modulating cytokines secretion, towards a $T_H2$ pattern (i.e., major increase in IL10).

EXAMPLE 3

Materials and methods are the same as Example 1.

MS EAE model: experimental autoimmune encephalomyelitis, SJL mice 7-8 weeks old were injected in the tail base with 1:1 of 200 µg proteolytic protein peptide (PLP) together with 200 µg CFA and IFA (containing *mycobacterium tuberculosis*). On the same day and two days later, mice were injected IP with 250 ng pertussis toxin. Within nine days, animals started developing paralysis. PIF-1 was administered using a subcutaneously implanted Alzet® pump at 0.75 mg/kg/day for 28 days and its effect was compared to a control group. Daily monitoring of the degree of paralysis (grade 0/no disease-5/dead animal) occurred up to 40 days. PIF-1's protective effects were calculated using the Mann-Whitney non parametric test.

MS model. We further examined whether PIF-1 therapy could be effective in an additional autoimmune model, experimental autoimmune encephalomyelitis (EAE) in which the majority of the damage occurs in poorly accessible region of the body, the central nervous system. By exposing mice to a combination of a toxic agent (PLP) for the nervous system together with boosting further the inflammatory response with two additional types of bacterial-toxins led to rapid paralysis <10 days. The exposure to PIF-1 at 0.75 mg/kg/day for 28 days led to a continuous protection by significantly reducing the paralysis score, as determined by daily observations using a clinical score. The protective effect also lasted for at least two weeks after stopping therapy (P<0.002).

The experimental myeloencephalitis, EAE, is recognized as a highly relevant and acute model for MS. The exposure to auto-antigens coupled by induction with two bacterial immunogens leads to progressive paralysis within short term. We found that PIF-1 led to a significant reduction in the paralysis score across the observation period which persisted even two weeks after cessation of therapy. This is an indication that autoimmune neurological disorders may be alleviated by PIF-1. Additionally, histological examination demonstrated that PIF treated mice were protected against inflammation of the spinal cord v. control (data not shown).

MS is believed to be the result of a genetic predisposition followed by a viral insult that leads to CD4+ autoreactive cells followed by differentiation to the $T_H1$ phenotype. On the other hand, local damage to central nervous system may occur by CD8+ T cells, and other elements that are involved in the innate immune system. This leads to altered $T_H2$ cytokines, regulatory T, and NK cells and IFN secretion. We have previously shown that several elements of this immune cascade are modulated by PIF-1, consequently, the tolerogenic peptide may be involved in one or more aspects of this immune disorder.

EXAMPLE 4

To determine maximally tolerated dose of PIF-1 in patients who develop GVHD after matched BMT, using an insulin pump. Recipients with grade II GVHD will be randomized into three groups: (1) continue conventional therapy (i.e., steroids and cyclosporin A), as control; (2) add PIF-1 therapy while continuing conventional therapy; and (3) stop conventional therapy and use PIF-1 alone. Patients will be continuously treated for 4 weeks (using an insulin pump), with 30% dose increments, 15 patients/group. Pre-therapy clinical indices, including tumor burden, will be compared to the same indices during/post PIF-1 exposure, monitoring skin for lesions and testing organ function, including PBMC ability to respond to mitogen challenge.

To examine PIF-1's effectiveness in GVHD prevention with maintained anticancer effect. Upon successful completion of the first study, BMT recipients will be randomized into three different groups: (1) conventional therapy (control); (2) conventional prophylaxis of GVHD combined with PIF-1; (3) PIF-1 prophylaxis alone. At transplant, patients will begin PIF-1 therapy (using an insulin pump) at 30% increments for 12 weeks followed by 3+ months observation, 15 patients/group. The number of patients that develop GVHD, the degree of the reaction, and response to cancer will be compared between the two test groups.

EXAMPLE 5

Assess effect of PIF on PBMC isolated from patients with Crohn's disease. Established patients PBMC(N=20) will be isolated and cultured in the presence of PIF alone using a dose dependent design and in presence of +/−PHA, or CD3MAb/CD28Mab, used as mitogens, using Cloning media, serum free. After 24 hours of exposure PBMC culture media will be collected and tested for a) cytokine release, both TH1 and TH2, using the Luminex 10 package b) PIF receptor expression exposing to FITC-PIF and labeled—CD14, CD4, CD8, or CD58, or CD19MAb followed by flow cytometry) c) in selective cases, mRNA will be extracted and using an Affymetrix chip global genome analysis will be carried out. Results will be compared with PBMC similarly treated derived from normal volunteers.

Assess effect of PIF on colon biopsy of patients with Chron's disease. In parallel, to obtaining PBMC also biopsies from the same patients will be obtained during colonoscopy. Biopsy samples will be placed in culture to generate explants using RPMI1640 medium. Explant cultures will be carried out for 24 hours in the presence of PIF 0-200 nM. Subsequently, the media will be collected and analyzed for cytokines using the 10 multiplex Luminex system (TH1 and TH2). The tissue itself will be placed in formalin and will be analyzed for cytokine content using IHC, as well as immune cell type presence using flow cytometry and specific CD markers.

Generate Polyclonal Antibodies to the Synthetic PIF-1, PIF-2 and PIF-3 Peptides To generate specific antibodies against sPIF-$1_{15}$ (SEQ ID NO: 13) conjugation to carrier, Keyhole Limpet hemocyanin (KLH) was carried out. sPIF-$1_{15}$ (SEQ ID NO: 13) was conjugated to KLH either on the carboxy or amine terminus of the molecule to cover potential differences in immunogenicity related to peptide presentation. The two peptide-carrier conjugates generated were injected into two rabbits. Within a 5-week immunization protocol all 4 rabbits responded by generating a high titer serum, with a titer of 1:50,000-1:150,000. The titer strength appeared to increase with the second bleeding. These rabbits may serve as a long-term reservoir of serum for antibody generation AbPIF-$1_{15}$. The rabbits may continue to be injected with immunogens on a monthly basis, collecting sera periodically and testing for titer and affinity. Antibodies to other PIFs, including AbPIF-$2_{13}$ and AbPIF-$3_{18}$, were generated with the same method using KLH bound peptide in the amine terminal. Rabbits bled 8 weeks after immunization yielded 1:25,000 titers for both peptides with detection of the PIF peptides to the nanomolar region. These antibodies were affinity purified using PIF-1, PIF-2 and PIF-3 bound affinity columns. The purified antibodies were conjugated each to a separate affinity column and they will serve for isolation of PIF peptides from various biological fluids.

Monoclonal antibodies to PIF-1 were developed as well. A hybridoma cell that produces a monoclonal antibody specific for a PIF polypeptide, and culturing the cell under conditions that permit production of the monoclonal antibody.

Such PIF antibodies may be used in assay as well as in therapeutic treatment (vaccination) of patients. For example, PIF peptide conjugates may be used as antigen (vaccine) to fight malaria. PIF itself, being a minimal unit might behave as a better antigen than the when its sequence is embedded in the intact, full length circumsporozoite protein in the malaria outer cell membrane. In another example, PIF antagonist (a peptide or other chemical shown to bind to PIF receptors, and block PIF function) or any procedure whereby such compound is used as drug, may be useful to treat malaria or block malaria propagation in the human body (by blocking the sites through/by which the parasite controls and paralyses the immune system and allows it to proliferate). Similarly, any humanized or horse antibodies to PIF or a procedure whereby these are used as agents may be used for passive immunization for malaria. (assuming such antibodies must recognize the circumsporozoite protein on the malaria parasite).

In one example, polyclonal antibodies AbPIF-$1_{15}$ were generated against sPIF-$1_{15}$ (SEQ ID NO: 13) in rabbits (Covance Inc.). High titers 50% at 1:50,000 were achieved. Serial dilutions of synthetic sPIF-$1_{15}$ (SEQ ID NO: 13) were plated, blocked and then washed off. PIF-1 antibody (1:5000) was added incubated and washed off. Goat anti-rabbit antibody was added, incubated and washed off. Reaction was stopped by SDS and counted in plate reader (Biosynthesis Inc, G Vandydriff). As shown in the ELISA standard curve, PIF antibody detects low sPIF levels (pg). The antibody affinity was also confirmed by using a competition analysis between biotin labeled and unlabeled nPIF-$1_{15}$ (SEQ ID NO: 1) (data not shown). Also when scrPIF-1 (SEQ ID NO: 5) was tested in the assay the antibody did not recognize it attesting to the high specificity of the antibody that was generated.

Figure 5A:
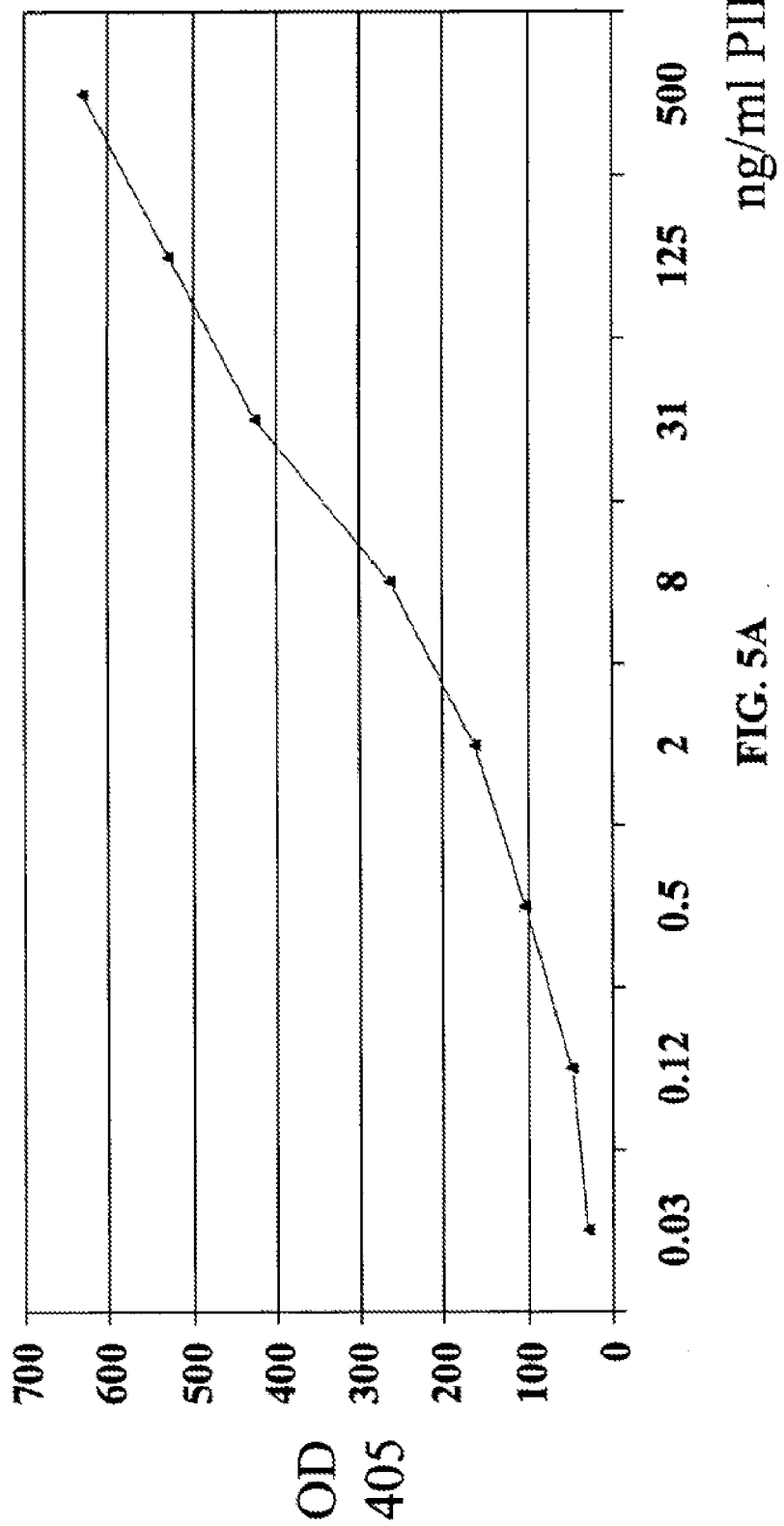
FIG. 5A. sPIF-115 (SEQ ID NO: 13) ELISA standard curve PIF antibody detects low sPIF levels (pg). Polyclonal antibodies AbPIF-115 were generated against sPIF-115 (SEQ ID NO: 13) in rabbits (Covance Inc.). High titers 50% at 1:50,000 were achieved. Serial dilutions of synthetic sPIF-115 (SEQ ID NO: 13) were plated, blocked and then washed off. PIF-1 antibody (1:5000) was added incubated and washed off. Goat anti-rabbit antibody was added, incubated and washed off. Reaction was stopped by SDS and counted in plate reader (Biosynthesis Inc, G Vandydriff). The antibody affinity was also confirmed by using a competition analysis between biotin labeled and unlabeled sPIF-115 (SEQ ID NO: 13) (data not shown). Also, when scrPIF-1 (SEQ ID NO: 5) was tested in the assay the antibody did not recognize it attesting to the high specificity of the antibody that was generated. Similar dose dependent results in the ELISA were obtained with affinity purified PIF-2 and PIF-3 antibodies (dilutions of the antibody up to 25,600) with linearity to the 30 pM of the peptide.

FIG. 5A demonstrates the affinity of PIF-1 IgY antibodies. Peptide as test antigen. Affi-pure IgY as the primary antibody and goat anti-Ig-Y as the secondary antibody. A fixed amount of antigen (5 ug/ml) and serial dilution of IgY.

Figure 5B:
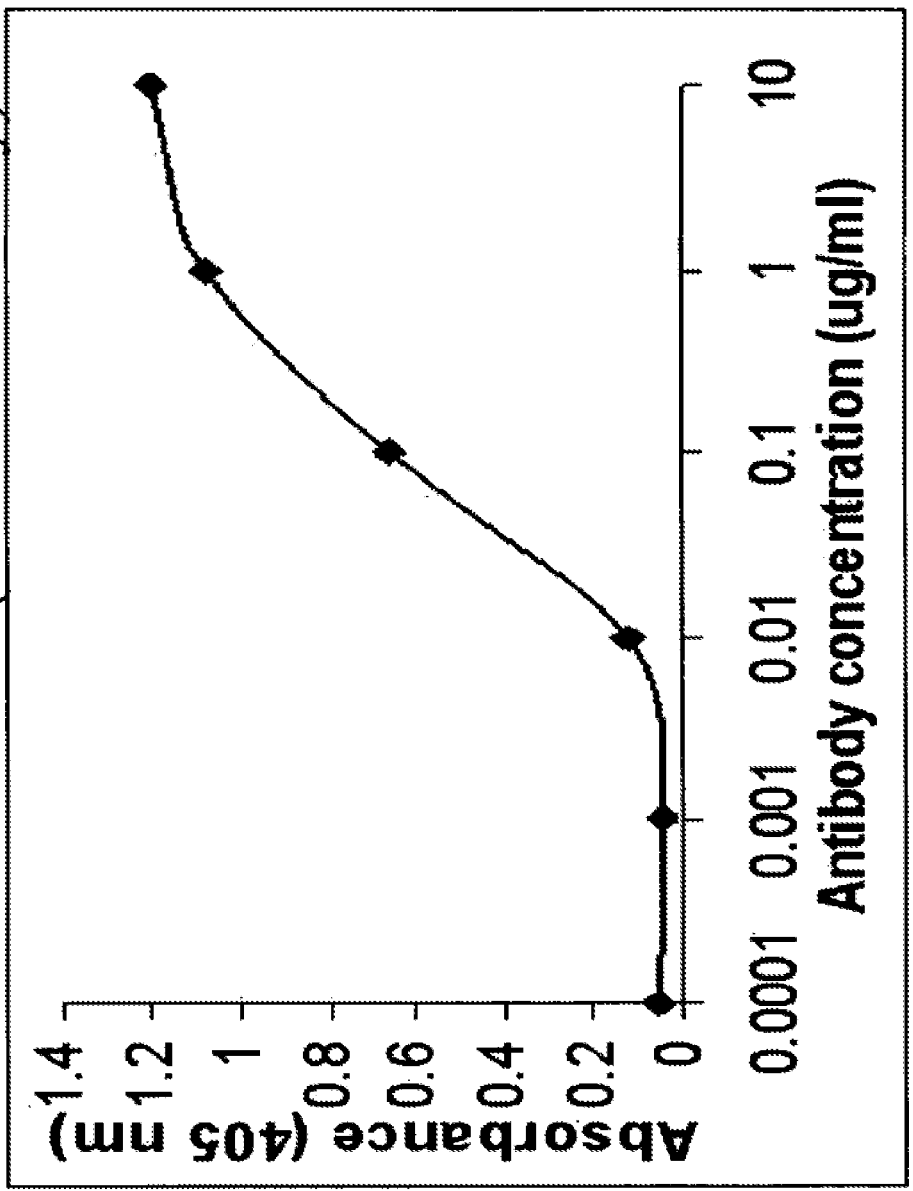
FIG. 5B shows ELISA profile of high affinity PIF-1 IgY antibodies (sandwich assay). Chicken were injected with KLH bound PIF-1 and the eggs were collected and affinity purified on a PIF column.

FIG. 5B demonstrates the specificity of PIF-1 polyclonal antibody. At 4.5 ug/ml pAb coating concentration, PIF-$1_{15}$ was detectable at 10-30 pM in a dose response curve with an $IC_{50}$ of 500-700 pm, and linearly up to 30 nM. scrPIF-1 did not compete with biotinylated peptide, as the native. No binding appears to occur on uncoated plates, yielding a good background. Results demonstrate that PIF-1 polyclonal antibody appears to avoid false positives and negatives.

In one non-limiting embodiment, a PIF-based pregnancy diagnosis utlilizing an ELISA or yes/no stick in the form of a kit is provided. The components of the PIF ELISA kit may include, for example, HRP-Avidin, PIF-Biotin and anti-PIF-$1_{15}$ antibody. In the absence of PIF in the test sample, HRP enzyme would bind to the antibody through the PIF-biotin complex, generating a maximum color. In the presence of PIF in the test sample, PIF binds to the PIF antibody and prevents the HRP enzyme complex from binding, generating a minimum color.

Figure 6:
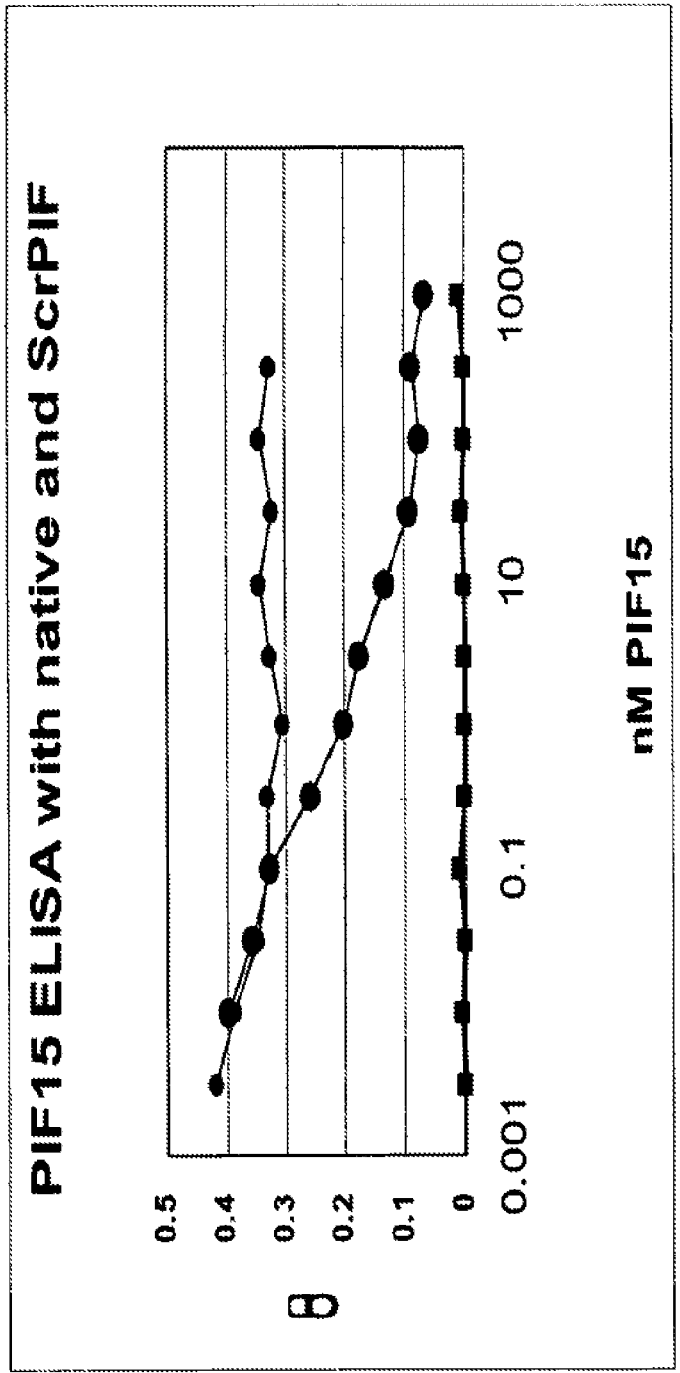
FIG. 6 shows ELISA profile of nPIF-115 and scrPIF-115 using Biotin labeled versus unlabeled peptide where the antibody captures the peptide in the unknown samples and compares it to standards (see FIG. 7).
Figure 7:
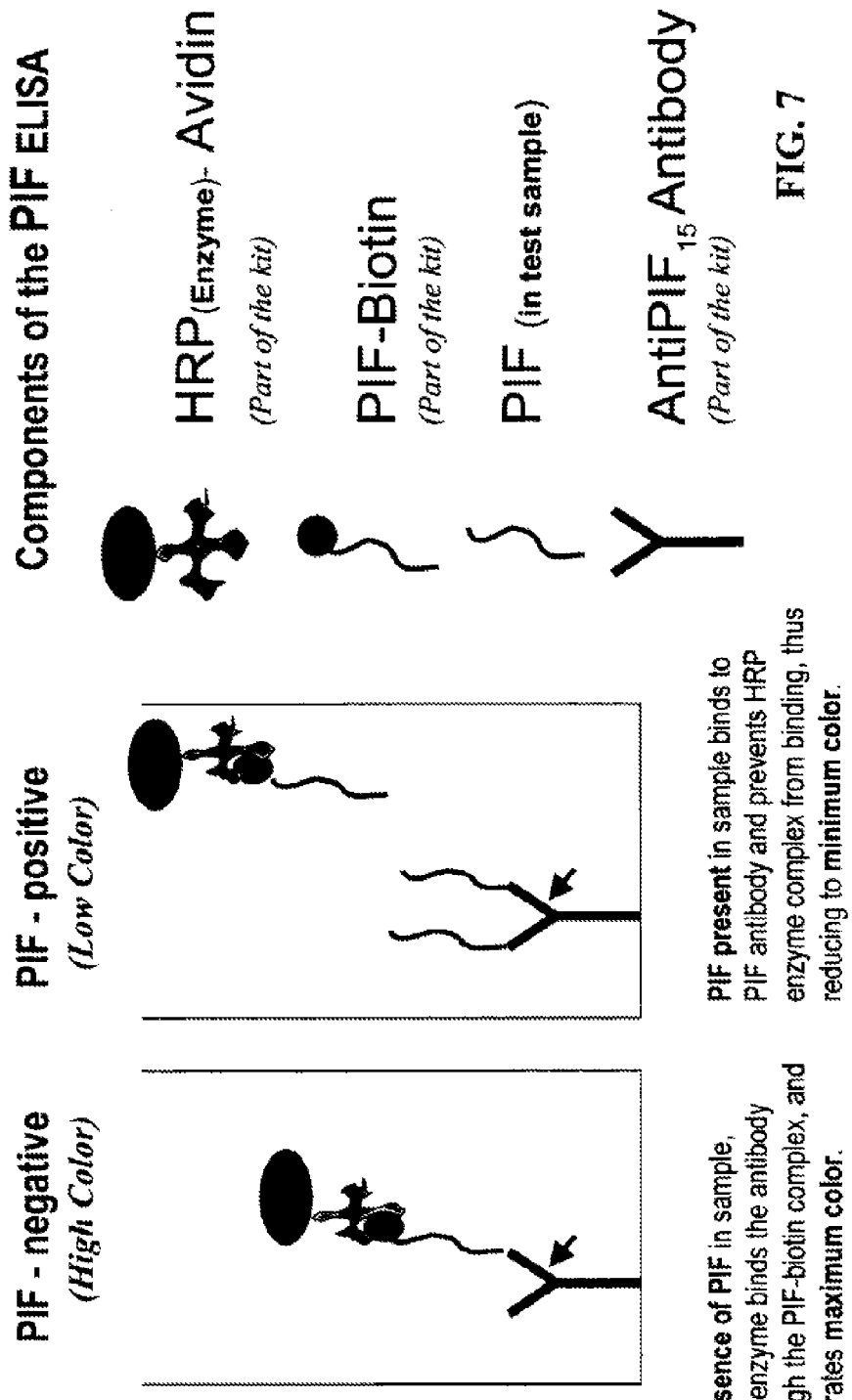
FIG. 7 depicts an example of a PIF-based diagnostic of the present invention. Four clones of monoclonal antibodies to PIF-115 were developed as well in mice and ascites fluid was generated with high affinity antibodies as hybridomas with sustained MAb production.

Isolation and Identification of PIF Like Proteins in Human Placenta and Other Fetal Tissues Using affinity purified PIF IgG 1, 2 and 3 and Igy PIF-1, PIFs were identified in human term placenta using Western blot. Human placenta was the test antigen. Lanes 1 and 3 were loaded with 50 ug of antigen per lane and lanes 2, 4 and 5 were loaded with 100 ug of antigen per lane. Lanes 1 and 2 were incubated with affi-pure anti-PIF-1 igY in a 1:50 dilution, goat anti-IgY-HRP in a 1:1000 dilution. Lane 3 was incubated with anti-PIF-1 antibody in 1:200 dilution. Lane 4 was incubated with anti-PIF-2 antibody in 1:50 dilution. Lane 5 was incubated with anti-PIF-3 antibody in 1:50 dilution and goat/anti-rabbit-HRP in a dilution of 1:1000. Results of western blot are shown in FIG. 6.

Expression of PIF-1 in human pregnancy tissues was examined using affinity purified IgG using immunohistochemistry methods. Intense trophoblastic expression was found in first and second trimester placenta while expression was low at term. With respect to the 14-18 weeks fetus using a tissue array (60 samples, covering practically all organs). The highest expression was in the spleen and liver, with lesser in the adrenal, stomach and small bowel with no detectable expression in the esophagus and several other organs. The presence of PIF was also measured in the adrenal tissue, stomach, small bowel, thyroid and other organs (not shown). Non relevant IgG was used as controls.

Overall this indicates that PIF-1 is expressed in the human placenta and fetus across gestation where it declines at term to facilitate the process of delivery by lowering maternal tolerance for the fetus. With respect for the fetus highest expression are found in hemopoietic organs where immune reaction is expected to be the highest.

In another example, PIF-1 associated proteins were identified in human placental tissue. Term human placental homogenates were passed through an affinity column of PIF-1 antibody. The mass spectrometry profile following elution by PIF-1 antibody affinity column. Various PIF-1 associated proteins were identified and sequenced following affinity chromatography, including (NM_000039) apolipoprotein A-I precursor [Homo sapiens], electron-transferring-flavoprotein dehydrogenase, (BC017165) similar to triosephosphate isomerase 1 [Homo sapiens], (NM_052925) leukocyte receptor cluster (LRC) member [Homo sapiens], (NM_018141) mitochondrial ribosomal protein S10; mitochondrial 28S ribosomal protein S10 [Homo sapiens], (NM_000518) beta globin [Homo sapiens], (BC012292) heat shock 27 kDa protein 1, stress responsive, estrogen regulated [Homo sapiens] P04792.40, Estradiol beta 1 dehydrogenase 1 P14061.13, Fetal Beta MHC binding factor Q 14297.01, microtubule-associated protein 1A (proliferation-related protein p80 P78559.40). Some of those proteins were not previously described in the placenta. The proteins sequenced appear to show roles in immune function, cytoskeleton, enzyme function, and protein synthesis and cell proliferation. None of the sequenced proteins have sequence homology with PIF-1, therefore it likely reflects, in some cases, that PIF is attached to these proteins reflecting a protein-protein interaction related to the peptides function.

Demonstration that PIF is Present in the Placenta of Sheep

Figure 8:
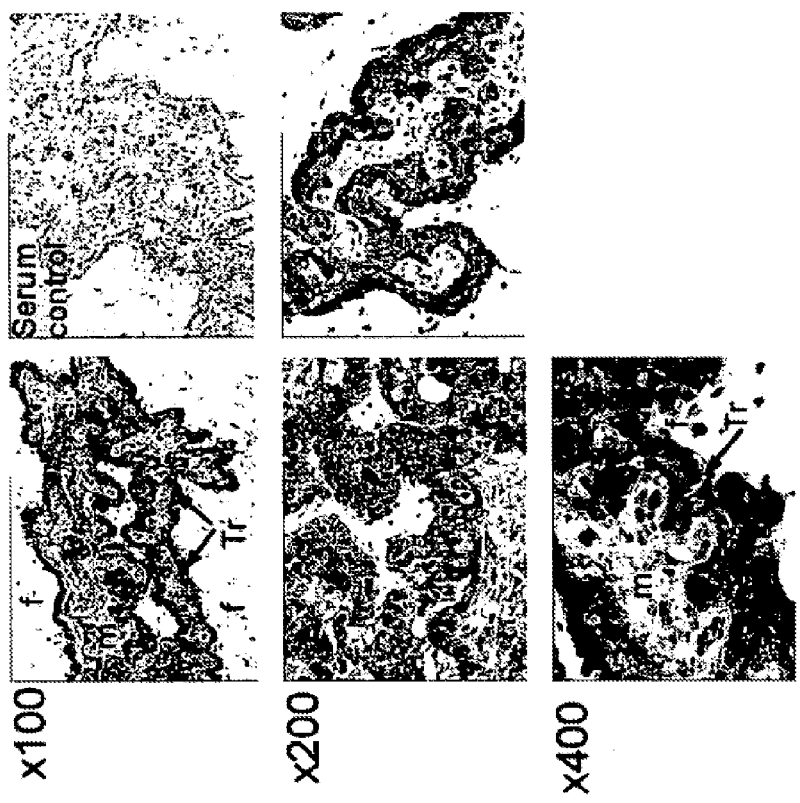
FIG. 8. nPIF-115 (SEQ ID NO: 1) is present in the ovine placenta, as demonstrated by immunocytochemistry methods. AbPIF-115 was exposed to placental tissue derived from a midtrimester ovine fetus. Compared to the non-specific staining by rabbit IgG, the PIF has shown intense staining of the fetal portion of the placenta.
Figure 9:
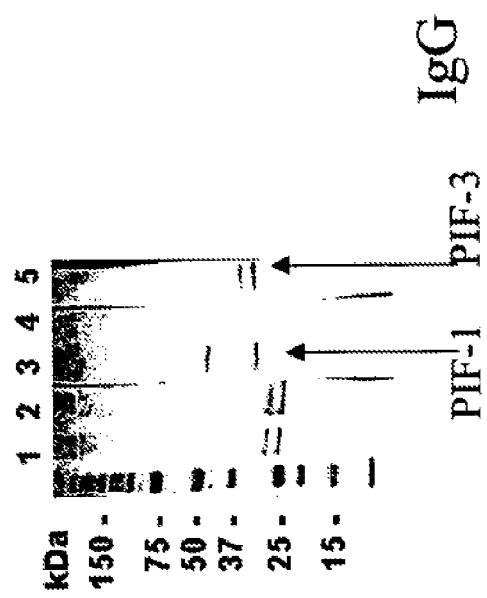
FIG. 9. Human term placental extracts were prepared (Dr Jerry Feitelson, GenWay, Inc) and were exposed to PIF antibodies using Western blot analysis, PIF like molecules were stained and the bands obtained were compared to a serial molecular weight standards run in parallel. Results showed that a number of PIF-1 related proteins are present at the 15-40 kDa range PIF-3 had a lower intensity with and was associated with different molecular weight bands. Finally, PIF-2 expression was minimal. This supports the notion that the human placenta may have precursor proteins from which by cleavage PIF peptides are produced. This also supports that view that PIF like molecules are present throughout pregnancy. Finally, it documents that in terms of intensity of expression in human by far PIF-1 is the most relevant at term.

Placental tissues were collected from a mid-gestation sheep fetus. The placenta was embedded in paraffin and slides were prepared. Representative slides exposed to the 1/100 dilution of rabbit AbPIF-$1_{15}$ antibody. Compared with the non immunized serum, AbPIF-$1_{15}$ antibody intensely stained the placenta, as shown in FIG. 8. The DAKO Chemmate system on the autostainer with DAB as the substrate was used. Moreover, the binding was highly specific since no adjacent maternal tissues appeared to be stained by the antibody. As such, AbPIF-$1_{15}$ antibody as well as AbPIF-$2_{13}$ and AbPIF-$3_{18}$ could be useful in identifying presence of PIF in pregnant tissues. Gestational changes: Visual analysis was carried out on day 50 (n=4), day 80 (n=7), day 100 (n=7), day 128 (n=4) and day 135 (n=8) 9Term=145 days). Based on visual assessment of percent staining, placental levels were highest at day 50 and then declined to day 80 after which they remained constant. This pattern reflected the observations that were made with the human placenta.

In terms of localization, PIF-1 is localized to the ovine maternal-fetal interface which is comprised of fetal trophoblast and maternal epithelium. Interestingly, PIF-1 is localized to the binucleate trophoblast cells. These are non-proliferative migratory cells which fuse with the maternal epithelium to form a hybrid maternal-fetal syncytium. On many of the slides there appears to be epithelial staining. Some of this may come from the fetal contribution to this layer. Later in gestation, the staining becomes more restricted to the binucleate trophoblastic cell population.

PIF-1 expression decreases at term of growth restricted fetuses. A comparison of the placental growth restricted group (n=14) to the controls (n=14) at day 80 (placental growth period) gave no significant differences. In late gestation, there is evidence of a decrease in PIF1 in the growth restricted group compared with controls.

Preliminary Study: PIF-1 Antibody and Scrambled PIF-1 Intravenous Administration is Non Toxic The contraceptive effect of either 150 ug of PIF-1scr in DMSO or 10 ug affinity purified PIF-1 (10 animals per group) or 20% DMSO solution (used as controls) was tested using single daily intravenous injections (Dr Alan Hoberman, Argus, Inc). Female mice were placed with male mice on the 3rd day afternoon of the expected estrus. Mating was confirmed by the presence of sperm in the vagina or a copulatory plug the next morning. Subsequently, were injected for 5 days one injection/day. Mice were sacrificed at day 12 of presumed gestation and Caesarean-sectioned. Corpora lutea, implantation sites and number of live and dead embryos were recorded. 2/10 mice in the PIF-1a and PIF-1 antibody group did not get pregnant, while in the control group all mice were pregnant. The effect was all or none since no toxic or teratogenic effects were noted in the mice that conceived.

Although the present invention has been described in considerable detail with reference to certain preferred embodiments thereof, other versions are possible. Therefore the spirit and scope of the appended claims should not be limited to the description and the preferred versions contain within this specification.

What is claimed is:

1. An antibody that binds specifically to PIF polypeptide comprising the amino acid sequence of SEQ ID NO: 1, SEQ ID NO: 3, SEQ ID NO: 4, SEQ ID NO: 6, SEQ ID NO: 7, SEQ ID NO: 10, or SEQ ID NO: 12.

2. The antibody of claim 1, wherein the antibody is a polyclonal antibody, and wherein the antibody binds a PIF polypeptide comprising an amino acid sequence selected from the group consisting of SEQ ID NO:1, SEQ ID NO:7, and SEQ ID NO:10.

3. The antibody of claim 1, wherein the antibody comprises a monoclonal or polyclonal antibody.

4. A composition for detecting the presence of PIF peptide in a fluid, the composition comprising:
   PIF antibodies; and
   the fluid,
   wherein the PIF antibodies bind a PIF polypeptide comprising an amino acid sequence selected from the group consisting of SEQ ID NO: 1, SEQ ID NO: 3, SEQ ID NO: 4, SEQ ID NO: 6, SEQ ID NO: 7, SEQ ID NO: 10, SEQ ID NO: 12, and combinations thereof.

5. The composition of claim 4, wherein the fluid is selected from the group consisting of serum, blood, urine, milk, saliva, embryo culture media, gestational tissues, fetal tissue and combinations thereof.

6. The composition of claim 4, wherein the antibodies are labeled.

7. The composition of claim 4, wherein the antibodies are chemically bonded to a substrate.

8. The composition of claim 4, wherein the antibodies comprise a monoclonal or polyclonal antibody.

9. The antibody of claim 1, wherein the half maximal inhibitory concentration is from about 500 pM to about 700 pM.

10. A method of assaying PIF in a sample comprising, obtaining a sample from a subject, mixing the sample with a detecting antibody and measuring the concentration of PIF in the sample.

11. The method of claim 10, wherein the antibody assay, is an ELISA.

12. The method of claim 11, wherein the assay is a sandwich ELISA.

* * * * *

SEQUENCE LISTING

<160> NUMBER OF SEQ ID NOS: 19

<210> SEQ ID NO 1
<211> LENGTH: 15
<212> TYPE: PRT

```
<213> ORGANISM: Homo sapiens

<400> SEQUENCE: 1

Met Val Arg Ile Lys Pro Gly Ser Ala Asn Lys Pro Ser Asp Asp
1               5                   10                  15

<210> SEQ ID NO 2
<211> LENGTH: 15
<212> TYPE: PRT
<213> ORGANISM: Homo sapiens

<400> SEQUENCE: 2

Met Val Arg Ile Lys Tyr Gly Ser Tyr Asn Lys Pro Ser Asp
1               5                   10                  15

<210> SEQ ID NO 3
<211> LENGTH: 13
<212> TYPE: PRT
<213> ORGANISM: Homo sapiens

<400> SEQUENCE: 3

Met Val Arg Ile Lys Pro Gly Ser Ala Asn Lys Pro Ser
1               5                   10

<210> SEQ ID NO 4
<211> LENGTH: 9
<212> TYPE: PRT
<213> ORGANISM: Homo sapiens

<400> SEQUENCE: 4

Met Val Arg Ile Lys Pro Gly Ser Ala
1               5

<210> SEQ ID NO 5
<211> LENGTH: 15
<212> TYPE: PRT
<213> ORGANISM: Artificial
<220> FEATURE:
<223> OTHER INFORMATION: Synthetic, scrambled amino acid sequence from
      region of Circumsporozoite protein Malaria

<400> SEQUENCE: 5

Gly Arg Val Asp Pro Ser Asn Lys Ser Met Pro Lys Asp Ile Ala
1               5                   10                  15

<210> SEQ ID NO 6
<211> LENGTH: 10
<212> TYPE: PRT
<213> ORGANISM: Homo sapiens

<400> SEQUENCE: 6

Ser Gln Ala Val Gln Glu His Ala Ser Thr
1               5                   10

<210> SEQ ID NO 7
<211> LENGTH: 13
<212> TYPE: PRT
<213> ORGANISM: Homo sapiens

<400> SEQUENCE: 7

Ser Gln Ala Val Gln Glu His Ala Ser Thr Asn Met Gly
1               5                   10

<210> SEQ ID NO 8
<211> LENGTH: 13
```

```
<212> TYPE: PRT
<213> ORGANISM: Artificial
<220> FEATURE:
<223> OTHER INFORMATION: Synthetic, scrambled amino acid sequence from
      region of retinoid and thyroid hormone receptor SMRT

<400> SEQUENCE: 8

Glu Val Ala Gln His Ser Gln Ala Ser Thr Met Asn Gly
1               5                   10

<210> SEQ ID NO 9
<211> LENGTH: 14
<212> TYPE: PRT
<213> ORGANISM: Artificial
<220> FEATURE:
<223> OTHER INFORMATION: Synthetic, scrambled amino acid sequence of
      human PIF-2[sub (14)]

<400> SEQUENCE: 9

Gly Gln Ala Ser Ser Ala Gln Met Asn Ser Thr Gly Val His
1               5                   10

<210> SEQ ID NO 10
<211> LENGTH: 18
<212> TYPE: PRT
<213> ORGANISM: Homo sapiens

<400> SEQUENCE: 10

Ser Gly Ile Val Ile Tyr Gln Tyr Met Asp Asp Arg Tyr Val Gly Ser
1               5                   10                  15

Asp Leu

<210> SEQ ID NO 11
<211> LENGTH: 11
<212> TYPE: PRT
<213> ORGANISM: Artificial
<220> FEATURE:
<223> OTHER INFORMATION: Synthetic, scrambled amino acid sequence from
      region of Circumsporozoite protein Malaria

<400> SEQUENCE: 11

Gly Met Arg Glu Leu Gln Arg Ser Ala Asn Lys
1               5                   10

<210> SEQ ID NO 12
<211> LENGTH: 9
<212> TYPE: PRT
<213> ORGANISM: Homo sapiens

<400> SEQUENCE: 12

Val Ile Ile Ile Ala Gln Tyr Met Asp
1               5

<210> SEQ ID NO 13
<211> LENGTH: 15
<212> TYPE: PRT
<213> ORGANISM: Artificial
<220> FEATURE:
<223> OTHER INFORMATION: Synthetic human PIF-1[sub(15)]

<400> SEQUENCE: 13

Met Val Arg Ile Lys Pro Gly Ser Ala Asn Lys Pro Ser Asp Asp
1               5                   10                  15

<210> SEQ ID NO 14
<211> LENGTH: 13
```

```
<212> TYPE: PRT
<213> ORGANISM: Artificial
<220> FEATURE:
<223> OTHER INFORMATION: Synthetic human PIF-2[sub(13)]

<400> SEQUENCE: 14

Ser Gln Ala Val Gln Glu His Ala Ser Thr Asn Met Gly
1               5                   10

<210> SEQ ID NO 15
<211> LENGTH: 18
<212> TYPE: PRT
<213> ORGANISM: Artificial
<220> FEATURE:
<223> OTHER INFORMATION: Synthetic human PIF-3[sub(18)]

<400> SEQUENCE: 15

Ser Gly Ile Val Ile Tyr Gln Tyr Met Asp Asp Arg Tyr Val Gly Ser
1               5                   10                  15

Asp Leu

<210> SEQ ID NO 16
<211> LENGTH: 9
<212> TYPE: PRT
<213> ORGANISM: Artificial
<220> FEATURE:
<223> OTHER INFORMATION: Synthetic human PIF-1[sub(9)]

<400> SEQUENCE: 16

Met Val Arg Ile Lys Pro Gly Ser Ala
1               5

<210> SEQ ID NO 17
<211> LENGTH: 9
<212> TYPE: PRT
<213> ORGANISM: Artificial
<220> FEATURE:
<223> OTHER INFORMATION: Synthetic human PIF-4[sub(9)]

<400> SEQUENCE: 17

Val Ile Ile Ile Ala Gln Tyr Met Asp
1               5

<210> SEQ ID NO 18
<211> LENGTH: 5
<212> TYPE: PRT
<213> ORGANISM: Artificial
<220> FEATURE:
<223> OTHER INFORMATION: Synthetic human PIF-1[sub(5)]

<400> SEQUENCE: 18

Met Val Arg Ile Lys
1               5

<210> SEQ ID NO 19
<211> LENGTH: 4
<212> TYPE: PRT
<213> ORGANISM: Artificial
<220> FEATURE:
<223> OTHER INFORMATION: Synthetic human PIF-1[sub(4)]

<400> SEQUENCE: 19

Pro Gly Ser Ala
1
```